US007118901B2

(12) United States Patent  
Suppmann et al.

(10) Patent No.: US 7,118,901 B2  
(45) Date of Patent: Oct. 10, 2006

(54) RECOMBINANT BOVINE PANCREATIC DESOXYRIBONUCLEASE I WITH HIGH SPECIFIC ACTIVITY

(75) Inventors: Bernhard Suppmann, Weilheim (DE); Johann-Peter Thalhofer, Weilheim (DE); Stephanie Ronning, Göttingen (DE); Helmut Schoen, Penzberg (DE); Rainer Müller, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 239 days.

(21) Appl. No.: 10/737,601

(22) Filed: Dec. 16, 2003

(65) Prior Publication Data

US 2004/0259197 A1 Dec. 23, 2004

(30) Foreign Application Priority Data

Dec. 18, 2002 (EP) ................................. 02028115  
Jan. 20, 2003 (EP) ................................. 03001213

(51) Int. Cl.  
C12N 9/22 (2006.01)

(52) U.S. Cl. ...................................... 435/199
(58) Field of Classification Search ................ None  
See application file for complete search history.

(56) References Cited

U.S. PATENT DOCUMENTS

| 4,683,293 A | 7/1987 | Craig |
| 4,808,537 A | 2/1989 | Stroman et al. |
| 4,812,405 A | 3/1989 | Lair et al. |
| 4,818,700 A | 4/1989 | Cregg et al. |
| 4,837,148 A | 6/1989 | Cregg |
| 4,855,231 A | 8/1989 | Stroman et al. |
| 4,857,467 A | 8/1989 | Sreekrishna et al. |
| 4,870,008 A | 9/1989 | Brake |
| 4,879,231 A | 11/1989 | Stroman et al. |
| 4,882,279 A | 11/1989 | Cregg |
| 4,885,242 A | 12/1989 | Cregg |
| 4,895,800 A | 1/1990 | Tschopp et al. |
| 4,929,555 A | 5/1990 | Cregg et al. |
| 5,002,876 A | 3/1991 | Sreekrishna et al. |
| 5,004,688 A | 4/1991 | Craig et al. |
| 5,032,516 A | 7/1991 | Cregg |
| 5,122,465 A | 6/1992 | Cregg et al. |
| 5,135,868 A | 8/1992 | Cregg |
| 5,166,329 A | 11/1992 | Cregg |
| 5,324,639 A | 6/1994 | Brierley et al. |
| 5,618,676 A | 4/1997 | Hitzeman et al. |
| 5,707,828 A | 1/1998 | Sreekrishna et al. |
| 5,854,018 A | 12/1998 | Hitzeman et al. |
| 5,856,123 A | 1/1999 | Hitzeman et al. |
| 5,919,651 A | 7/1999 | Hitzeman et al. |

FOREIGN PATENT DOCUMENTS

| EP | 0 116 201 | 8/1984 |
| EP | 0 301 669 | 6/1993 |
| EP | 0 853 121 | 7/1998 |
| EP | 1 122 306 | 8/2001 |
| WO | WO 90/07572 | 7/1990 |
| WO | WO 96/26278 | 8/1996 |
| WO | WO 00/56903 | 9/2000 |

OTHER PUBLICATIONS

Beck, E., Ludwig, G., Auerswald, E.A., Reiss, B., Schaller, H., "Nucleotide sequence and exact localization of the neomycin phosphotransferase gene from transposon Tn5", Gene, 19 (1982), pp. 327-336.

Chen, C.Y., Lu, S.C., Liao, T.H., "Cloning, sequencing and expression of a cDNA encoding bovine pancreatic deoxyribonuclease I in *Escherichia coli*: purification and characterization of the recombinant enzyme", Gene 206 (1998), 181-184.

Calmels, T., Parriche, M., Durand, H., Tiraby, G., "High efficiency transformation of *Tolypocladium geodes* conidiospores to phleomycin resistance", Curr Genet (1991) 20:309-314.

Chen, X.J., Fukuhara, H., "A gene fusion system using the aminoglycoside 3' -phosphotransferase gene of the kanamycin-resistance transposon Tn903: use in the yeasts *Kluyveromyces lactis* and *Saccharomyces cerevisiae*", Gene, 69 (1988) 181-192 Elsevier.

Drocourt, D., Calmels, T., Reynes, J.P., Baron, M., Tiraby, G. "Cassettes of the *Streptoalloteichus hindustanus ble* gene for transformation of lower and higher eukaryotes to phleomycin resistance", Nucleic Acids Research, vol. 18, No. 13, 1990 Oxford University Press, 4009.

Funakoshi, A., Tsubota, Y., Fujii, K., Ibayashi, H., Takagi, Y., "Simple Purification and Properties of Bovine Pancreatic Deoxyribonuclease I", J. Biochem. 88, 1113-1118 (1980).

Julius, D., Schekman, R., Thorner, J., "Glycosylation and Processing of Prepro-a-Factor through the Yeast Secretory Pathway", Cell, vol. 36, Feb. 1984, 309-318.

Liao, T.H., "Deoxyribonuclease I and its Clinical Applications", J. Formos Med Assoc 1997, vol. 96, No. 7, pp. 481-487.

Kunitz, M., "Crystalline Desoxyribonuclease, I. Isolation and General Properties Spectrophotometric Method for the Measurement of Desoxyribonuclease Activity", Publication from Oct. 3, 1949, Laboratoroies of the Rockefeller Institute for Medical Research, Princeton, NJ, pp. 349-362.

Lazarides, E., Lindberg, U., "Actin Is the Naturally Occurring Inhibitor of Deoxyribonuclease I", Proc. Nat. Acad. Sci. USA, vol. 71, No. 12, pp. 4742-4746, Dec. 1974.

(Continued)

Primary Examiner—Charles L. Patterson, Jr.  
(74) Attorney, Agent, or Firm—Marilyn L. Amick; Roche Diagnostics Operations, Inc.

(57) ABSTRACT

A method is provided for the production of a bovine pancreatic protein with a specific desoxyribonuclease activity of at least 6,000 units per mg of protein. Methylotrophic yeast is used as a heterologous host organism. The bovine pancreatic protein is secreted into the growth medium from which it is purified.

19 Claims, 4 Drawing Sheets

OTHER PUBLICATIONS

Liao, T.H., "Multiple forms of deoxyribonuclease I", Molecular and Cellular Biochemistry 34, 15-22 (1981).

Nefsky, B., Bretscher, A. "Preparation of immobilized monomeric actin and its use in the isolation of protease-free and ribuonuclease-free pancreatic deoxyribonuclease I", Eur. J. Biochem. 179, (1989) 215-219.

Mizuno, K., Nakamura, T., Takada, K., Sakakibara; S., Matsuo, H. "A Membrane-Bound, Calcium-Dependent Protease in Yeast a-Cell Cleaving on the Carboxyl Side of Paired Basic Residues", Biochemical and Biophysical Research Communications, vol. 144, No. 2, 1987, pp. 807-814.

Southern, P.J., Berg, P., "Transformation of Mammalian Cells to Antibiotic Resistance with a Bacterial Gene Under Control of the SV40 Early Region Promotor", Journal of Molecular and Applied Genetics, 1:327-341, 1982.

Nishikawa, A., Mizuno, S., "The efficiency of N-linked glycosylation of bovine DNase I depends on the Asn-Xaa-Ser/Thr sequence and the tissue of origin", Biochem J. (2001) 355; 245-248.

Van Treeck, U., Schmidt, F., Wiedemann, B., "Molecular Nature of a Streptomycin and Sulfonamide Resistance Plasmid (pBP1) Prevalent in Clinical *Escherichia coli* Strains and Integration of an Ampicillin Resistance Transposon (TnA)", Antimicrobial Agents and Chemotherapy, Mar. 1981, pp. 371-380.

Vedvick, T., Buckholz, G., Engel, M., Urcan, M., Kinney, J., Provow, S., Siegel, R.S., Thill, G.P., "High-level secretion of biologically active aprotinin from the yeast *Pichia pastoris*", Journal of Industrial Microbiology, 7 (1991) 197-202.

Nishikawa, A., Gregory, W., Frenz, J., Cacia, J., Kornfeld, S., "The Phosphorylation of Bovine DNase I Asn-linked Oligosaccharides Is Dependent on Specific Lysine and Arginine Residues", The Journal of Biological Chemistry, vol. 272, No. 31, Aug. 1, 1997, pp. 19408-19412.

Werten, M.W., Van Den Bosch, T.J., Wind, R.D., Mooibroek, H., DeWolf, F.A., "High-yield Secretion of Recombinant Gelatins by *Pichia pastoris*", Yeast, 15, (1999) 1087-1096.

Pan, C.Q., Ulmer, J.S., Herzka, A., Lazarus, R.A., "Mutational analysis of human DNase I at the DNA binding interface: Implications for DNA recognition, catalysis, and metal ion dependence", Protein Science (1998) 7:628-636.

Paudel, H.K., Liao, T.H., "Purification, Characterization, and the Complete Amino Acid Sequence of Procine Pancreatic Deoxyribonuclease", The Journal of Biological Chemistry, vol. 261, No. 34, Dec. 5, 1986, pp. 16006-16011.

Shak, S., Capon, D.J., Hellmiss, R., Marsters, S.A., Baker, C.L., "Recombinant human DNase I reduces the viscosity of cystic fibrosis sputum", Proc. Natl. Acad. Sci. USA, vol. 87, Dec. 1990, pp. 9188-9192.

Worrall, A.F., Connolly, B.A., "The Chemical Synthesis of a Gene Coding for Bovine Pancreatic DNase I and Its Cloning and Expression in *Escherichia coli*", The Journal of Biological Chemistry, vol. 265, No. 35, Dec. 15, 1990, pp. 21889-21895.

SEQUENCE LISTING

<160> NUMBER OF SEQ ID NOS: 29

<210> SEQ ID NO 1
<211> LENGTH: 260
<212> TYPE: PRT
<213> ORGANISM: Bos taurus

<400> SEQUENCE: 1

Leu Lys Ile Ala Ala Phe Asn Ile Arg Thr Phe Gly Glu Thr Lys Met

-continued

```
                1               5                  10                 15
Ser Asn Ala Thr Leu Ala Ser Tyr Ile Val Arg Ile Val Arg Arg Tyr
                20                 25                 30
Asp Ile Val Leu Ile Gln Glu Val Arg Asp Ser His Leu Val Ala Val
                35                 40                 45
Gly Lys Leu Leu Asp Tyr Leu Asn Gln Asp Pro Asn Thr Tyr His
        50                 55                 60
Tyr Val Val Ser Glu Pro Leu Gly Arg Asn Ser Tyr Lys Glu Arg Tyr
65                  70                 75                 80
Leu Phe Leu Phe Arg Pro Asn Lys Val Ser Val Leu Asp Thr Tyr Gln
                85                 90                 95
Tyr Asp Asp Gly Cys Glu Ser Cys Gly Asn Asp Ser Phe Ser Arg Glu
                100                105                110
Pro Ala Val Lys Phe Ser Ser His Ser Thr Lys Val Lys Glu Phe
        115                120                125
Ala Ile Val Ala Leu His Ser Ala Pro Ser Asp Val Ala Glu Ile
        130                135                140
Asn Ser Leu Tyr Asp Val Tyr Leu Asp Val Gln Gln Lys Trp His Leu
145                 150                155                160
Asn Asp Val Met Leu Met Gly Asp Phe Asn Ala Asp Cys Ser Tyr Val
                165                170                175
Thr Ser Ser Gln Trp Ser Ser Ile Arg Leu Arg Thr Ser Ser Thr Phe
                180                185                190
Gln Trp Leu Ile Pro Asp Ser Ala Asp Thr Thr Ala Thr Ser Thr Asn
        195                200                205
Cys Ala Tyr Asp Arg Ile Val Val Ala Gly Ser Leu Leu Gln Ser Ser
        210                215                220
Val Val Pro Gly Ser Ala Ala Pro Phe Asp Phe Gln Ala Ala Tyr Gly
225                 230                235                240
Leu Ser Asn Glu Met Ala Leu Ala Ile Ser Asp His Tyr Pro Val Glu
                245                250                255
Val Thr Leu Thr
        260

<210> SEQ ID NO 2
<211> LENGTH: 282
<212> TYPE: PRT
<213> ORGANISM: Bos taurus

<400> SEQUENCE: 2

Met Arg Gly Thr Arg Leu Met Gly Leu Leu Ala Leu Ala Gly Leu
1               5                  10                 15
Leu Gln Leu Gly Leu Ser Leu Lys Ile Ala Ala Phe Asn Ile Arg Thr
                20                 25                 30
Phe Gly Glu Thr Lys Met Ser Asn Ala Thr Leu Ala Ser Tyr Ile Val
                35                 40                 45
Arg Ile Val Arg Arg Tyr Asp Ile Val Leu Ile Gln Glu Val Arg Asp
        50                 55                 60
Ser His Leu Val Ala Val Gly Lys Leu Leu Asp Tyr Leu Asn Gln Asp
65                  70                 75                 80
Asp Pro Asn Thr Tyr His Tyr Val Val Ser Glu Pro Leu Gly Arg Asn
                85                 90                 95
Ser Tyr Lys Glu Arg Tyr Leu Phe Leu Phe Arg Pro Asn Lys Val Ser
                100                105                110
```

```
Val Leu Asp Thr Tyr Gln Tyr Asp Asp Gly Cys Glu Ser Cys Gly Asn
        115                 120                 125

Asp Ser Phe Ser Arg Glu Pro Ala Val Val Lys Phe Ser Ser His Ser
        130                 135                 140

Thr Lys Val Lys Glu Phe Ala Ile Val Ala Leu His Ser Ala Pro Ser
145                 150                 155                 160

Asp Ala Val Ala Glu Ile Asn Ser Leu Tyr Asp Val Tyr Leu Asp Val
                165                 170                 175

Gln Gln Lys Trp His Leu Asn Asp Val Met Leu Met Gly Asp Phe Asn
            180                 185                 190

Ala Asp Cys Ser Tyr Val Thr Ser Ser Gln Trp Ser Ser Ile Arg Leu
        195                 200                 205

Arg Thr Ser Ser Thr Phe Gln Trp Leu Ile Pro Asp Ser Ala Asp Thr
        210                 215                 220

Thr Ala Thr Ser Thr Asn Cys Ala Tyr Asp Arg Ile Val Val Ala Gly
225                 230                 235                 240

Ser Leu Leu Gln Ser Ser Val Val Pro Gly Ser Ala Ala Pro Phe Asp
                245                 250                 255

Phe Gln Ala Ala Tyr Gly Leu Ser Asn Glu Met Ala Leu Ala Ile Ser
            260                 265                 270

Asp His Tyr Pro Val Glu Val Thr Leu Thr
        275                 280

<210> SEQ ID NO 3
<211> LENGTH: 286
<212> TYPE: PRT
<213> ORGANISM: Bos taurus

<400> SEQUENCE: 3

Met Arg Gly Thr Arg Leu Met Gly Leu Leu Leu Ala Leu Ala Gly Leu
1               5                   10                  15

Leu Gln Leu Gly Leu Ser Leu Glu Lys Arg Leu Lys Ile Ala Ala Phe
                20                  25                  30

Asn Ile Arg Thr Phe Gly Glu Thr Lys Met Ser Asn Ala Thr Leu Ala
            35                  40                  45

Ser Tyr Ile Val Arg Ile Val Arg Arg Tyr Asp Ile Val Leu Ile Gln
    50                  55                  60

Glu Val Arg Asp Ser His Leu Val Ala Val Gly Lys Leu Leu Asp Tyr
65                  70                  75                  80

Leu Asn Gln Asp Asp Pro Asn Thr Tyr His Tyr Val Val Ser Glu Pro
                85                  90                  95

Leu Gly Arg Asn Ser Tyr Lys Glu Arg Tyr Leu Phe Leu Phe Arg Pro
            100                 105                 110

Asn Lys Val Ser Val Leu Asp Thr Tyr Gln Tyr Asp Asp Gly Cys Glu
        115                 120                 125

Ser Cys Gly Asn Asp Ser Phe Ser Arg Glu Pro Ala Val Val Lys Phe
    130                 135                 140

Ser Ser His Ser Thr Lys Val Lys Glu Phe Ala Ile Val Ala Leu His
145                 150                 155                 160

Ser Ala Pro Ser Asp Ala Val Ala Glu Ile Asn Ser Leu Tyr Asp Val
                165                 170                 175

Tyr Leu Asp Val Gln Gln Lys Trp His Leu Asn Asp Val Met Leu Met
            180                 185                 190

Gly Asp Phe Asn Ala Asp Cys Ser Tyr Val Thr Ser Ser Gln Trp Ser
        195                 200                 205
```

-continued

```
Ser Ile Arg Leu Arg Thr Ser Ser Thr Phe Gln Trp Leu Ile Pro Asp
    210                 215                 220

Ser Ala Asp Thr Thr Ala Thr Ser Thr Asn Cys Ala Tyr Asp Arg Ile
225                 230                 235                 240

Val Val Ala Gly Ser Leu Leu Gln Ser Ser Val Pro Gly Ser Ala
                245                 250                 255

Ala Pro Phe Asp Phe Gln Ala Ala Tyr Gly Leu Ser Asn Glu Met Ala
                260                 265                 270

Leu Ala Ile Ser Asp His Tyr Pro Val Glu Val Thr Leu Thr
                275                 280                 285

<210> SEQ ID NO 4
<211> LENGTH: 345
<212> TYPE: PRT
<213> ORGANISM: artificial sequence
<220> FEATURE:
<223> OTHER INFORMATION: Bovine pancreatic DNase I; modified bovine
      pre-protein

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Leu Lys Ile Ala Ala Phe Asn Ile Arg Thr Phe
                85                  90                  95

Gly Glu Thr Lys Met Ser Asn Ala Thr Leu Ala Ser Tyr Ile Val Arg
                100                 105                 110

Ile Val Arg Arg Tyr Asp Ile Val Leu Ile Gln Glu Val Arg Asp Ser
            115                 120                 125

His Leu Val Ala Val Gly Lys Leu Leu Asp Tyr Leu Asn Gln Asp Asp
130                 135                 140

Pro Asn Thr Tyr His Tyr Val Val Ser Glu Pro Leu Gly Arg Asn Ser
145                 150                 155                 160

Tyr Lys Glu Arg Tyr Leu Phe Leu Phe Arg Pro Asn Lys Val Ser Val
                165                 170                 175

Leu Asp Thr Tyr Gln Tyr Asp Asp Gly Cys Glu Ser Cys Gly Asn Asp
                180                 185                 190

Ser Phe Ser Arg Glu Pro Ala Val Val Lys Phe Ser Ser His Ser Thr
            195                 200                 205

Lys Val Lys Glu Phe Ala Ile Val Ala Leu His Ser Ala Pro Ser Asp
    210                 215                 220

Ala Val Ala Glu Ile Asn Ser Leu Tyr Asp Val Tyr Leu Asp Val Gln
225                 230                 235                 240

Gln Lys Trp His Leu Asn Asp Val Met Leu Met Gly Asp Phe Asn Ala
                245                 250                 255

Asp Cys Ser Tyr Val Thr Ser Ser Gln Trp Ser Ser Ile Arg Leu Arg
                260                 265                 270

Thr Ser Ser Thr Phe Gln Trp Leu Ile Pro Asp Ser Ala Asp Thr Thr
```

```
              275                 280                 285
Ala Thr Ser Thr Asn Cys Ala Tyr Asp Arg Ile Val Val Ala Gly Ser
    290                 295                 300

Leu Leu Gln Ser Ser Val Val Pro Gly Ser Ala Ala Pro Phe Asp Phe
305                 310                 315                 320

Gln Ala Ala Tyr Gly Leu Ser Asn Glu Met Ala Leu Ala Ile Ser Asp
                325                 330                 335

His Tyr Pro Val Glu Val Thr Leu Thr
            340                 345

<210> SEQ ID NO 5
<211> LENGTH: 783
<212> TYPE: DNA
<213> ORGANISM: artificial sequence
<220> FEATURE:
<223> OTHER INFORMATION: Nucleotide sequence encoding secreted bovine
      pancreatic DNase I, i.e., the protein without signal peptide

<400> SEQUENCE: 5
ttgaagattg ctgctttcaa cattagaact ttcggtgaaa ctaaaatgtc taacgctact     60
ttggcatctt acatcgttag aattgtcaga agatatgata tcgttttaat tcaagaagtt    120
agagactctc acttggttgc agttggtaaa ttgttagact acttgaacca agatgaccca    180
aacacttacc actacgttgt ttctgaacca ttgggtagaa actcttacaa agaaagatac    240
ttattcttgt tcagaccaaa caaagtttca gttttggata cttaccaata cgacgacggt    300
tgcgaatctt gtggtaacga ttctttctcc agagaacctg ctgttgttaa attctcatca    360
cactctacca aggttaaaga gttcgctatc gttgctttgc attctgctcc ttctgacgct    420
gttgctgaaa ttaactcttt gtacgacgtt tacttagatg ttcaacgaaa atggcacttg    480
aacgacgtca tgttgatggg tgactttaac gctgattgct cttatgttac ttcttctcaa    540
tggtcttcaa ttagattgag aacatcttca actttccaat ggttaattcc tgattccgct    600
gataccactg ctactagtac caactgtgct tacgatagaa tcgttgttgc tggatcatta    660
ttgcaatctt ctgttgtccc aggttcagcg gccccttttcg atttccaagc tgcatatggt    720
ttgtctaatg aaatggcttt agccatttct gatcactacc cagttgaagt cacattgaca    780
taa                                                                   783

<210> SEQ ID NO 6
<211> LENGTH: 66
<212> TYPE: DNA
<213> ORGANISM: artificial sequence
<220> FEATURE:
<223> OTHER INFORMATION: Nucleotide sequence encoding the native bovine
      signal peptide sequence of the DNase I pre-protein nucleic acid
      sequence

<400> SEQUENCE: 6
atgagaggta ctagattgat gggtttgtta ttagctttgg ctggtttatt acaattaggt     60
ttgtct                                                                66

<210> SEQ ID NO 7
<211> LENGTH: 78
<212> TYPE: DNA
<213> ORGANISM: artificial sequence
<220> FEATURE:
<223> OTHER INFORMATION: Nucleotide sequence encoding the native bovine
      signal peptide sequence of the DNase I pre-protein and an
      additional signal peptidase cleavage site
```

```
<400> SEQUENCE: 7
atgagaggta ctagattgat gggtttgtta ttagctttgg ctggtttatt acaattaggt    60
ttgtctctcg agaagaga                                                  78

<210> SEQ ID NO 8
<211> LENGTH: 255
<212> TYPE: DNA
<213> ORGANISM: Saccharomyces cerevisiae

<400> SEQUENCE: 8
atgagatttc cttcaattttt tactgctgtt ttattcgcag catcctccgc attagctgct   60
ccagtcaaca ctacaacaga agatgaaacg gcacaaattc cggctgaagc tgtcatcggt   120
tactcagatt tagaagggga tttcgatgtt gctgttttgc cattttccaa cagcacaaat   180
aacgggttat tgtttataaa tactactatt gccagcattg ctgctaaaga agaagggtgta  240 tctctcgaga agaga                                                    255

<210> SEQ ID NO 9
<211> LENGTH: 72
<212> TYPE: DNA
<213> ORGANISM: artificial sequence
<220> FEATURE:
<223> OTHER INFORMATION: Synthetic primer

<400> SEQUENCE: 9
gcgcctcgag aagagattga agattgctgc tttcaacatt agaactttcg gtgaaactaa   60
aatgtctaac gc                                                        72

<210> SEQ ID NO 10
<211> LENGTH: 67
<212> TYPE: DNA
<213> ORGANISM: artificial sequence
<220> FEATURE:
<223> OTHER INFORMATION: Synthetic primer

<400> SEQUENCE: 10
cgatatcata tcttctgaca attctaacga tgtaagatgc caaagtagcg ttagacattt   60
tagattc                                                              67

<210> SEQ ID NO 11
<211> LENGTH: 69
<212> TYPE: DNA
<213> ORGANISM: artificial sequence
<220> FEATURE:
<223> OTHER INFORMATION: Synthetic primer

<400> SEQUENCE: 11
gtcagaagat atgatatcgt tttaattcaa gaagttagag actctcactt ggttgcagtt   60
ggtaaattg                                                            69

<210> SEQ ID NO 12
<211> LENGTH: 62
<212> TYPE: DNA
<213> ORGANISM: artificial sequence
<220> FEATURE:
<223> OTHER INFORMATION: Synthetic primer

<400> SEQUENCE: 12
cgtagtggta agtgtttggg tcatcttggt tcaagtagtc taacaattta ccaactgcaa   60
cc                                                                   62
```

<210> SEQ ID NO 13
<211> LENGTH: 72
<212> TYPE: DNA
<213> ORGANISM: artificial sequence
<220> FEATURE:
<223> OTHER INFORMATION: Synthetic primer

<400> SEQUENCE: 13
ccaaacactt accactacgt tgtttctgaa ccattgggta gaaactctta caaagaaaga     60
tacttattct tg                                                        72

<210> SEQ ID NO 14
<211> LENGTH: 72
<212> TYPE: DNA
<213> ORGANISM: artificial sequence
<220> FEATURE:
<223> OTHER INFORMATION: Synthetic primer

<400> SEQUENCE: 14
ccaaacactt accactacgt tgtttctgaa ccattgggta gaaactctta caaagaaaga     60
tacttattct tg                                                        72

<210> SEQ ID NO 15
<211> LENGTH: 63
<212> TYPE: DNA
<213> ORGANISM: artificial sequence
<220> FEATURE:
<223> OTHER INFORMATION: Synthetic primer

<400> SEQUENCE: 15
ggatacttac caatacgacg acggttgcga atcttgtggt aacgattctt tctccagaga     60
acc                                                                  63

<210> SEQ ID NO 16
<211> LENGTH: 68
<212> TYPE: DNA
<213> ORGANISM: artificial sequence
<220> FEATURE:
<223> OTHER INFORMATION: Synthetic primer

<400> SEQUENCE: 16
cgaactcttt aaccttggta gagtgtgatg agaatttaac aacagcaggt tctctggaga    60
aagaatcg                                                             68

<210> SEQ ID NO 17
<211> LENGTH: 58
<212> TYPE: DNA
<213> ORGANISM: artificial sequence
<220> FEATURE:
<223> OTHER INFORMATION: Synthetic primer

<400> SEQUENCE: 17
ccaaggttaa agagttcgct atcgttgctt tgcattctgc tccttctgac gctgttgc     58

<210> SEQ ID NO 18
<211> LENGTH: 67
<212> TYPE: DNA
<213> ORGANISM: artificial sequence
<220> FEATURE:
<223> OTHER INFORMATION: Synthetic primer

<400> SEQUENCE: 18

```
gccatttctg ttgaacatct aagtaaacgt cgtacaaaga gttaatttca gcaacagcgt    60
cagaagg                                                              67
```

<210> SEQ ID NO 19
<211> LENGTH: 62
<212> TYPE: DNA
<213> ORGANISM: artificial sequence
<220> FEATURE:
<223> OTHER INFORMATION: Synthetic primer

<400> SEQUENCE: 19

```
gatgttcaac agaaatggca cttgaacgac gtcatgttga tgggtgactt taacgctgat    60
tg                                                                   62
```

<210> SEQ ID NO 20
<211> LENGTH: 65
<212> TYPE: DNA
<213> ORGANISM: artificial sequence
<220> FEATURE:
<223> OTHER INFORMATION: Synthetic primer

<400> SEQUENCE: 20

```
gttctcaatc taattgaaga ccattgagaa gaagtaacat aagagcaatc agcgttaaag    60
tcacc                                                                65
```

<210> SEQ ID NO 21
<211> LENGTH: 64
<212> TYPE: DNA
<213> ORGANISM: artificial sequence
<220> FEATURE:
<223> OTHER INFORMATION: Synthetic primer

<400> SEQUENCE: 21

```
gtcttcaatt agattgagaa catcttcaac tttccaatgg ttaattcctg attccgctga    60
tacc                                                                 64
```

<210> SEQ ID NO 22
<211> LENGTH: 63
<212> TYPE: DNA
<213> ORGANISM: artificial sequence
<220> FEATURE:
<223> OTHER INFORMATION: Synthetic primer

<400> SEQUENCE: 22

```
agcaacaacg attctatcgt aagcacagtt ggtactagta gcagtggtat cagcggaatc    60
agg                                                                  63
```

<210> SEQ ID NO 23
<211> LENGTH: 62
<212> TYPE: DNA
<213> ORGANISM: artificial sequence
<220> FEATURE:
<223> OTHER INFORMATION: Synthetic primer

<400> SEQUENCE: 23

```
cgatagaatc gttgttgctg gatcattatt gcaatcttct gttgtcccag gttcagcggc    60
cc                                                                   62
```

<210> SEQ ID NO 24
<211> LENGTH: 66
<212> TYPE: DNA
<213> ORGANISM: artificial sequence
<220> FEATURE:
<223> OTHER INFORMATION: Synthetic primer

<400> SEQUENCE: 24

| ggctaaagcc atttcattag acaaaccata tgcagcttgg aaatcgaaag gggccgctga | 60 |
|---|---|
| acctgg | 66 |

<210> SEQ ID NO 25
<211> LENGTH: 54
<212> TYPE: DNA
<213> ORGANISM: artificial sequence
<220> FEATURE:
<223> OTHER INFORMATION: Synthetic primer

<400> SEQUENCE: 25

| ctaatgaaat ggctttagcc atttctgatc actacccagt tgaagtcaca ttga | 54 |
|---|---|

<210> SEQ ID NO 26
<211> LENGTH: 42
<212> TYPE: DNA
<213> ORGANISM: artificial sequence
<220> FEATURE:
<223> OTHER INFORMATION: Synthetic primer

<400> SEQUENCE: 26

| cgcgtctaga gcggccgctt atgtcaatgt gacttcaact gg | 42 |
|---|---|

<210> SEQ ID NO 27
<211> LENGTH: 73
<212> TYPE: DNA
<213> ORGANISM: artificial sequence
<220> FEATURE:
<223> OTHER INFORMATION: Synthetic primer

<400> SEQUENCE: 27

| cgaaaaatga gaggtactag attgatgggt tgttattag ctttggctgg tttattacaa | 60 |
|---|---|
| ttaggtttgt ctc | 73 |

<210> SEQ ID NO 28
<211> LENGTH: 75
<212> TYPE: DNA
<213> ORGANISM: artificial sequence
<220> FEATURE:
<223> OTHER INFORMATION: Synthetic primer

<400> SEQUENCE: 28

| tcgagagaca aacctaattg taataaacca gccaaagcta ataacaaacc catcaatcta | 60 |
|---|---|
| gtacctctca ttttt | 75 |

<210> SEQ ID NO 29
<211> LENGTH: 938
<212> TYPE: DNA
<213> ORGANISM: Pichia pastoris

<400> SEQUENCE: 29

| agatctaaca tccaaagacg aaaggttgaa tgaaaccttt ttgccatccg acatccacag | 60 |
|---|---|
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggccccctg gcgaggttca tgtttgttta | 300 |

-continued

```
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaa                            938
```

RECOMBINANT BOVINE PANCREATIC DESOXYRIBONUCLEASE I WITH HIGH SPECIFIC ACTIVITY

BACKGROUND OF THE INVENTION

The present invention relates to the production of recombinant bovine pancreatic desoxyribonuclease I in methylotrophic yeast. In particular, the present invention relates to a bovine pancreatic desoxyribonuclease I that is secreted by the methylotrophic yeast into the growth medium from which it is purified. Also provided are use and kits of the recombinant bovine pancreatic desoxyribonuclease I.

Bovine pancreatic desoxyribonuclease I is an industrial product with a wide range of applications. For instance, applications in the field of cell biology make use of bovine pancreatic desoxyribonuclease I in standard laboratory procedures for the purpose of dissociating cell tissue and isolating single cells. Such processes are always accompanied by rupture and lysis of some cells. As a consequence, DNA is released from these cells into the intercellular space and/or the dissociation medium and causes unwanted cell clumping. Adding bovine pancreatic desoxyribonuclease I to the dissociation medium is a preferred means to prevent unwanted cell clumping as the enzyme has been shown not to be cytotoxic in concentrations of up to 1 mg/ml. Thus, cell clumping is prevented by hydrolysing DNA. For purposes of tissue culture, bovine pancreatic desoxyribonuclease I is also used in combination with other enzymes such as collagenase or trypsin (Kaighn, M. E., In: Tissue culture, methods and applications; Kruse, P. F. & Patterson, M. K., eds., Academic Press, New York & London, 1973, 54–58).

Regarding the fields of molecular biology and nucleic acid biochemistry, bovine pancreatic desoxyribonuclease I is used in applications such as nick translation, the production of random DNA fragments, desoxyribonuclease I protection assays such as transcription factor footprinting, removal of DNA template after in vitro transcription, removal of DNA from RNA samples prior to applications such as RT-PCR, and removal of DNA from other preparations generated by biological and/or biochemical procedures, to name but a few (Sambrook, Fritsch & Maniatis, Molecular Cloning, A Laboratory Manual, 3rd edition, CSHL Press, 2001). Thus, removal of DNA is effected by hydrolysing DNA.

DNase I is also used in medical applications aimed at reducing the viscoelasticity of pulmonary secretions (Liao, T. H., J. Formos. Med. Assoc. 96 (1997) 481–487). Whereas for this particular purpose desoxyribonuclease I of human origin is the preferred enzyme, desoxyribonuclease I from bovine pancreas is preferred for the different kinds of research use exemplified above. Thus, bovine pancreatic desoxyribonuclease I is an enzyme that is produced in an industrial scale and sold as a regular industrial product (e.g. desoxyribonuclease I from bovine pancreas EC 3.1.21.1, Item No. 1284932 in the 2002 catalogue of Roche Diagnostics GmbH, Mannheim).

Bovine pancreatic desoxyribonuclease I has a molecular weight of about 30,000 daltons and an enzymatic activity optimum at pH 7.8. Bovine pancreatic desoxyribonuclease I hydrolyses phosphodiester linkages of DNA, preferentially adjacent to a pyrimidine nucleotide yielding DNA molecules with a free hydroxyl group at the 3' position and a phosphate group at the 5' position. The average chain length of a limit digest is a tetranucleotide. There are four desoxyribonucleases derived from bovine pancreas which are all glycoproteins. They differ from each other either in a carbohydrate side chain or polypeptide component. Bovine pancreatic desoxyribonuclease I has diverse chemical activity acting upon single stranded DNA, double stranded DNA and chromatin (Liao, T. H., Mol. Cell Biochem. 34 (1981) 15–22). Similarly to other desoxyribonucleases, bovine pancreatic desoxyribonuclease I appears to be modulated in vivo by actin which is taking the effect as a cellular inhibitor (Lazarides, E., and Lindberg, U., Proc. Natl. Acad. Sci. USA 71 (1974) 4742). Moreover, like other desoxyribonucleases, bovine pancreatic desoxyribonuclease I is activated by divalent metal ions. Maximum activation is attained with $Mg^{2+}$ and $Ca^{2+}$. A metallosubstrate, such as a magnesium salt of DNA is necessary. Citrate completely inhibits magnesium-activated but not manganese-activated desoxyribonuclease I. Desoxyribonuclease I is inhibited by chelating agents such as EDTA, and by sodium dodecyl sulfate (Sambrook, Fritsch & Maniatis, Molecular Cloning, A Laboratory Manual, 3rd edition, CSHL Press, 2001).

When desoxyribonuclease activity is quantified, the present document refers to "units". Thus, the nucleolytic activity of bovine pancreatic desoxyribonuclease I is quantified using a photometric assay similar to Kunitz, M. (J. Gen. Physiol. 33 (1950) 349–62 and 363). The "specific desoxyribonuclease activity" or "specific activity" of a given preparation is defined as the number of units per mg of potein in the preperation, determined by the method described in detail in Example 12.

A "methylotrophic yeast" is defined as a yeast that is capable of utilising methanol as its carbon source. The term also comprises laboratory strains thereof. In case a methylotrophic yeast strain is auxotrophic and because of this needs to be supplemented with an auxiliary carbon-containing substance such as, e.g. histidine in the case of a methylotrophic yeast strain unable to synthesise this amino acid in sufficient amounts, this auxiliary substance is regarded as a nutrient but not as a carbon source.

A "vector" is defined as DNA which can comprise, i.e. carry and maintain the DNA fragment of the invention, including, for example, phages and plasmids. These terms are understood by those of skill in the art of genetic engineering. The term "expression cassette" denotes a nucleotide sequence encoding a pre-protein, operably linked to a promoter and a terminator. As for vectors containing an expression cassette, the terms "vector" and "expression vector" are synonyms.

The term "oligonucleotide" is used for a nucleic acid molecule, DNA (or RNA), with less than 100 nucleotides in length.

"Transformation" means introducing DNA into an organism so that the DNA is replicable, either as an extrachromosomal element or by chromosomal integration.

The term "expression" and the verb "to express" denote transcription of DNA sequences and/or the translation of the transcribed mRNA in a host organism resulting in a pre-protein, i.e. not including post-translational processes.

A nucleotide sequence "encodes" a peptide or protein when at least a portion of the nucleic acid, or its complement, can be directly translated to provide the amino acid sequence of the peptide or protein, or when the isolated nucleic acid can be used, alone or as part of an expression vector, to express the peptide or protein in vitro, in a prokaryotic host cell, or in a eukaryotic host cell.

A "promoter" is a regulatory nucleotide sequence that stimulates transcription. These terms are understood by those of skill in the art of genetic engineering. Like a promoter, a "promoter element" stimulates transcription but constitutes a sub-fragment of a larger promoter sequence.

The term "operably linked" refers to the association of two or more nucleic acid fragments on a single vector so that the function of one is affected by the other. For example, a promoter is operably linked with a coding sequence, i.e. a nucleotide sequence encoding a protein or a pre-protein, when it is capable of affecting the expression of that coding sequence, i.e., that the coding sequence is under the transcriptional control of the promoter.

The term "polypeptide" or "protein" denotes a polymer composed of more than 90 amino acid monomers joined by peptide bonds. The term "peptide" denotes an oligomer composed of 90 or fewer amino acid monomers joined by peptide bonds. A "peptide bond" is a covalent bond between two amino acids in which the α-amino group of one amino acid is bonded to the α-carboxyl group of the other amino acid.

The term "pre-protein" denotes a primary translation product that is a precursor of a mature protein, i.e. in this case a protein results from post-translational processing of a pre-protein.

The term "post-translational processing" denotes the modification steps a pre-protein is subjected to, in order result in a mature protein in a cellular or extracellular compartment.

A "signal peptide" is a cleavable signal sequence of amino acids present in the pre-protein form of a secretable protein. Proteins transported across the cell membrane, i.e. "secreted", typically have an N-terminal sequence rich in hydrophobic amino acids about 15 to 30 amino acids long. Sometime during the process of passing through the membrane, the signal sequence is cleaved by a signal peptidase (Alberts, B., Johnson, A., Lewis, J., Raff, M., Roberts, K., Walter, P. (eds), Molecular Biology of the Cell, fourth edition, 2002, Garland Science Publishing). Many sources of signal peptides are well known to those skilled in the art and can include, for example, the amino acid sequence of the α-factor signal peptide from *Saccharomyces cerevisiae* and the like. Another example is the bovine signal peptide of the native bovine pancreatic desoxyribonuclease I pre-protein. In general, the pre-protein N-terminus of essentially any secreted protein is a potential source of a signal peptide suitable for use in the present invention. A signal peptide can also be bipartite comprising two signal peptides directing the pre-protein to a first and a second cellular compartment. Bipartite signal peptides are cleaved off stepwise during the course of the secretory pathway. A specific example therefor is the prepro peptide of the α-factor from *Saccharomyces cerevisiae* (Waters et al., J. Biol. Chem. 263 (1988) 6209–14).

Pre-proteins with an N-terminal signal peptide are directed to enter the "secretory pathway". The secretory pathway comprises the processes of post-translational processing and finally results in secretion of a protein. Glycosylation and the formation of disulfide bonds are processes that are part of the secretory pathway prior to secretion. In the present document it is understood that proteins secreted by methylotrophic yeast strains have passed through the secretory pathway.

Until presently, a major source of bovine pancreatic desoxyribonuclease I is pancreatic tissue obtained from slaughtered cattle. The enzyme is usually purified from the tissue material using chromatographic separation techniques such as those described by Funakoshi, A., et al., J. Biochem. (Tokyo) 88 (1980) 1113–1138; Paudel, H. K., and Liao, T. H., J. Biol Chem. 261 (1986) 16006–16011; and Nefsky, B., and Bretscher, A., Eur. J. Biochem. 179 (1989) 215–219. The purification process under the conditions of a research laboratory yields a specific activitiy in the range of 1,000 units per mg of protein obtained from 400 g of tissue, as explicitly reported by Paudel, H. K., and Liao, T. H., J. Biol Chem. 261 (1986) 16006–16011. In an upscaled industrial process, the isolation of bovine pancreatic desoxyribonuclease I from bovine pancreatic tissue yields preparations of isolated enzyme which usually exhibit a specific activity of 3,500 units per mg of protein (our own unpublished observation). Commercial preparations of research-grade bovine pancreatic desoxyribonuclease I purified from bovine pancreas usually have a specific activity below this value as exemplified by Roche products (Roche Diagnostics GmbH, Mannheim, Germany; catalogue items as of November 2002) having the catalogue numbers 1284932 (2,000 units/mg), 104132 (3,000 units/mg), 104159 (2,000 units/mg), and Sigma-Aldrich products (Sigma-Aldrich Chemie GmbH, Taufkirchen, Germany; catalogue items as of November 2002) having the catalogue numbers D5025 (2,000 units/mg) D4263 (2,000 U/mg), D4513 (2,000 units/mg), DN-25 (400–800 units/mg). Generally, pancreas tissue as source for bovine pancreatic desoxyribonuclease I poses a problem as this tissue has a high content of other digestive pro-enzymes and their activated forms. On the one hand, the mixture from which the desired enzyme is purified is therefore very complex and requires elaborate separation techniques. On the other hand, proteases among the digestive enzymes may destroy the desired protein, especially during the first steps of the purification process when pancreatic tissue is homogenised. One could also speculate that pancreatic tissue homogenate contains inhibitory substances that inactivate a substantial portion of the bovine pancreatic desoxyribonuclease I, thereby limiting the specific activity of active enzyme that can be purified from this source.

It is also known to the art that recombinant expression of an enzymatically active bovine pancreatic desoxyribonuclease I protein in a bacterial host is possible. However, overexpression poses a problem owing to the intrinsic toxicity of an endonuclease for a bacterial cell. Apparently, toxicity is caused by intracellular degradation of host cell DNA with high levels of active bovine pancreatic desoxyribonuclease I enzyme being present in the bacterial cytoplasm. In a bacterial cell transcription and translation are tightly connected as opposed to eukaryotic cells where these processes take place in separate compartments, i.e. the nucleus and the cytoplasm. Thus, the selection of bacterial clones overexpressing bovine pancreatic desoxyribonuclease I at the same time promotes instability of these clones (e.g. genetic instability) and/or the recombinant desoxyribonuclease protein to be produced. Attempts to overcome this problem were mainly based on tightly regulated and inducible bacterial expression systems.

Worrall, A. F., and Connolly, B. A. (J. Biol. Chem. 265 (1990) 21889–21895) expressed an active bovine pancreatic desoxyribonuclease I protein in *E. coli* making use of a synthetic coding sequence adapted to the codon usage of the host organism. Transcriptional expression was under the control of the λpL promoter. The recombinant protein was produced intracellularly and afterwards solubilised by means of sonication. The recombinant active protein was found to be toxic for the bacterial host stain. Thus, expression yield was in the range between 100 μg to 1 mg/l culture. The specific activity of the recombinant active bovine pancreatic desoxyribonuclease I from *E. coli* was found to be identical to that of the native protein. The value given in the document ($5 \times 10^8$ units/g of protein) was not the true value of the preparation but was corrected for purity. The recombinant bovine pancreatic desoxyribonuclease I protein was purified only partially and the document is completely silent about the specific desoxyribonuclease activity of a substantially pure and/or research-grade product.

Chen, C. Y., et al. (Gene 206 (1998) 181–184) expressed in E. coli a cDNA representing the original bovine pancreatic transcript. The construct was expressed in the strain BL21(DE3)pLysE and transcribed by an IPTG-inducible T7 polymerase. However, overexpression of an active bovine pancreatic desoxyribonuclease I was found to be limited in quantity and the product appeared to be toxic for the bacterial host organism. Due to cell lysis upon induction, bovine pancreatic desoxyribonuclease I activity was found in the supernatant but also in the cellular fraction of the culture. desoxyribonuclease enzyme activity was measured using an assay for enzyme activity that differed from the Kunitz assay in that there are changes with respect to divalent cations and their concentration in the reaction buffer, as well as its pH. However, generally the units detected by this assay appear to be comparable to those of the Kunitz assay. According to the assay of this document, the approximate yield from the induced culture was 3,500 units/l. The specific enzyme activity of the recombinant bovine pancreatic desoxyribonuclease I produced in E. coli was 908 units/mg was in the same range as the specific activity of native bovine pancreatic desoxyribonuclease I purified in parallel from pancreatic tissue (938 units/mg).

As it is commonly observed when post-translationally processed proteins of eukaryotic origin are expressed in a prokaryotic host system, the bovine pancreatic desoxyribonuclease I obtained by means of recombinant expression in E. coli markedly differs from the native protein. Particularly N-glycosylation which is a hallmark of the native pancreatic desoxyribonuclease I protein is absent in the recombinant product derived from prokaryotic expression systems. Glycosylation does not take place in E. coli and the publications by Worrall, A. F., and Connolly, B. A., J. Biol. Chem. 265 (1990) 21889–21895 as well as Chen, C. Y., et al., Gene 206 (1998) 181–184, confirm that the recombinantly produced bovine pancreatic desoxyribonuclease I proteins were not glycosylated. Also, folding of the protein and the formation of disulfide bonds are controlled differently in eukaryotic cells (Alberts, B., Johnson, A., Lewis, J., Raff, M., Roberts, K., Walter, P. (eds), Molecular Biology of the Cell, fourth edition, 2002, Garland Science Publishing). Above all, the formation of disulfide bridges in the recombinantly produced protein can be assumed to occur randomly once SH groups of the protein come in contact with aerial oxygen.

Glycosylated bovine pancreatic desoxyribonuclease I also was expressed in cultured mammalian cells. Nishikawa, A., et al. (J. Biol. Chem. 272 (1997) 19408–19412) produced bovine pancreatic desoxyribonuclease I as well as human desoxyribonuclease I in COS-1 cells in order to study mannose phosphorylation of these proteins. The document is however completely silent regarding yield or activity of the recombinant desoxyribonuclease I produced. A further glycosylation study on bovine pancreatic desoxyribonuclease I was published by Nishikawa, A., and Mizuno, S., Biochem. J. 355 (2001) 245–248, dealing with the efficiency of N-linked glycosylation of bovine pancreatic desoxyribonuclease I. Also this document is completely silent regarding yield or activity of the recombinant desoxyribonuclease I produced.

Recombinant expression of human pancreatic desoxyribonuclease I in embryonic kidney 293 cells was described by Shak, S., Proc. Natl. Acad. Sci. USA 87 (1990) 9188–9192 as well as by the same author in WO 90/07572. In the latter document it is stated that the specific activity of recombinant human pancreatic desoxyribonuclease from 293 cells appeared to be comparable to that of bovine desoxyribonuclease (Sigma, product D5025) which was used as a reference. According to the supplier's (Sigma) catalogue the product has a specific activity of 2,000 units/mg which puts the recombinantly expressed human pancreatic desoxyribonuclease I protein in the same range. Moreover, according to the invention described in WO 90/07572, recombinant desoxyribonuclease is preferably expressed in mammalian cells but also in prokaryotes, fungi, yeast, pichia, insects and the like. However, apart from expression in mammalian cells the document does not disclose any other example for eukaryotic expression systems. Moreover, the document is completely silent regarding glycosylation, the formation of disulfide bridges and the specific activity of recombinant desoxyribonuclease when produced in other eukaryotic expression systems. Furthermore, the document is completely silent on the impact of secretion on the yield of the desired protein as well as on its activity.

Using a similar expression system as in WO 90/07572, WO 96/26278 describes the production of human desoxyribonuclease I variants that exhibit a reduced binding affinity to actin. EP 1 122 306 discloses the expression of a human desoxyribonuclease II in HeLa cells.

The methods that are provided by the state of the art to produce a bovine pancreatic protein with desoxyribonuclease activity have certain disadvantages. The present invention provides an improved method.

It is an object of the invention to provide a cost-effective alternative source for bovine pancreatic desoxyribonuclease I. It is a further object of the invention to purify bovine pancreatic desoxyribonuclease I as a recombinant protein synthesised by a non-animal host organism. It is another object of the invention to provide an expression system in which the host organism tolerates the recombinant bovine pancreatic desoxyribonuclease I better than bacteria. Another object of the invention is to provide an expression system which simplifies and accelerates the separation of bovine pancreatic desoxyribonuclease I from cellular or media components, therefore conserving enzyme activity which otherwise may be lost. Yet another object of the invention is to provide a production procedure that leads to an enzyme preparation with a high specific activity. Yet another object of the invention is that the production procedure is amenable to upscaling towards a cost-effective industrial process.

BRIEF SUMMARY OF THE INVENTION

It was surprisingly found that in case bovine pancreatic desoxyribonuclease I is recombinatly expressed in the form of a pre-protein in methylotrophic yeast, whereby the methylotrophic yeast secretes the mature protein, the purified protein has an exceptionally high specific activity, that is to say a specific activity equal or higher than 6,000 units per mg of protein.

Thus, according to the invention, there is provided a method to produce a bovine pancreatic protein with desoxyribonuclease activity, comprising the steps of (a) providing a vector comprising a nucleotide sequence that encodes a pre-protein consisting of the bovine pancreatic protein and a signal peptide, (b) transforming a methylotrophic yeast strain with the vector, (c) cultivating the transformed methylotrophic yeast strain in a growth medium that contains nutrients and methanol, whereby the methylotrophic yeast strain expresses and secretes the bovine pancreatic protein into the growth medium, and (d) purifying the bovine pancreatic protein from the growth medium, whereby the bovine pancreatic protein is bovine pancreatic desoxyribonuclease I, whereby the bovine pancreatic protein has desoxyribonuclease activity, and whereby the bovine pancreatic protein purified in step (d) is characterised by a specific desoxyribonuclease activity of at least 6,000 units per mg of protein.

Therefore, the product is defined as a bovine pancreatic protein, obtainable by the method comprising the steps of (a) providing a vector comprising a nucleotide sequence that encodes a pre-protein consisting of the bovine pancreatic protein and a signal peptide, (b) transforming a methylotrophic yeast strain with the vector, (c) cultivating the transformed methylotrophic yeast strain in a growth medium that contains nutrients and methanol, whereby the methylotrophic yeast strain expresses and secretes the bovine pancreatic protein into the growth medium, and (d) purifying the bovine pancreatic protein from the growth medium, whereby the bovine pancreatic protein is bovine pancreatic desoxyribonuclease I, whereby the bovine pancreatic protein has desoxyribonuclease activity, and whereby the bovine pancreatic protein is characterised by a specific desoxyribonuclease activity of at least 6,000 units per mg of protein.

DETAILED DESCRIPTION OF THE INVENTION

The enzyme bovine pancreatic desoxyribonuclease I is produced using methylotrophic yeast as a non-animal host organism. Methylotrophic yeasts have the biochemical pathways necessary for methanol utilization and are classified into four genera, based upon cell morphology and growth characteristics: *Hansenula*, *Pichia*, *Candida*, and *Torulopsis*. The most highly developed methylotrophic host systems utilize *Pichia pastoris* (*Komagataella pastoris*) and *Hansenula polymorpha* (*Pichia angusta*).

Expression of heterologous proteins in yeast is described in U.S. Pat. No. 5,618,676, U.S. Pat. No. 5,854,018, U.S. Pat. No. 5,856,123, and U.S. Pat. No. 5,919,651.

Yeast organisms produce a number of proteins that are synthesized intracellularly but have a function outside the cell. These extracellular proteins are referred to as secreted proteins. Initially the secreted proteins are expressed inside the cell in the form of a precursor or a pre-protein containing an N-terminal signal peptide ensuring effective direction of the expressed product into the secretory pathway of the cell, across the membrane of the endoplasmic reticulum. The signal peptide is generally cleaved off from the desired product during translocation. Cleavage is effected proteolytically by a signal peptidase. A particular sub-sequence of amino acids of the signal peptide is recognised and cleaved by the signal peptidase. This sub-sequence is referred to as signal peptidase cleavage site. Once having entered the secretory pathway, the protein is transported to the Golgi apparatus. From the Golgi apparatus the proteins are distributed to the plasma membrane, lysosomes and secretory vesicles.

Secreted proteins are confronted with different environmental conditions as opposed to intracellular proteins. Part of the processes of the secretory pathway is to stabilise the maturing extracellular proteins. Therefore, pre-proteins that are passed through the secretory pathway of yeast undergo specific posttranslational processing. For example, processing can comprise the generation of disulfide bonds to form intramolecular cross-links. Moreover, certain amino acids of the protein can be glycosylated.

Several approaches have been suggested for the expression and secretion in yeast of proteins heterologous to yeast. EP 0 116 201 describes a process by which proteins heterologous to yeast are transformed by an expression vector harboring DNA encoding the desired protein, a signal peptide and a peptide acting as a signal peptidase cleavage site. A culture of the transformed organism is prepared and grown, and the protein is recovered from culture media. For use in yeast cells a suitable signal peptide has been found to be the α-factor signal peptide from *Saccharomyces cerevisiae* (U.S. Pat. No. 4,870,008).

When the present invention was made it was found surprisingly that the bovine signal peptide of the native bovine pancreatic desoxyribonuclease I pre-protein is also sufficient to direct the pre-protein to the secretory pathway of methylotrophic yeast. Therefore, the bovine signal peptide of the native bovine pancreatic desoxyribonuclease I pre-protein can be used to express and secrete a heterologous gene product in methylotrophic yeast.

During secretion, the yeast enzyme KEX-2 is the signal peptidase which recognizes a Lysine-Arginine sequence as its cleavage site in the pre-protein. KEX-2 cleaves at the junction to the sequence of the desired protein. As a result, the desired gene product is released and free of the leader portions, i.e. the signal peptide of the pre-protein. KEX-2 endoprotease was originally characterised in *Saccharomyces* yeast where it specifically processes the precursor of mating type α-factor and a killer factor (Julius, D., et al., Cell 37 (1984) 1075–1089). Methylotrophic yeast species such as *Pichia pastoris* share the KEX-2-type protease (similar role and function) with *Saccharomyces cerevisiae* (Werten, M. W., et al., Yeast 15 (1999) 1087–1096).

A well-established methylotrophic yeast species exemplarily described as host for high-level recombinant protein expression is *Pichia pastoris* (U.S. Pat. No. 4,683,293, U.S. Pat. No. 4,808,537, U.S. Pat. No. 4,812,405, U.S. Pat. No. 4,818,700, U.S. Pat. No. 4,837,148, U.S. Pat. No. 4,855,231, U.S. Pat. No. 4,857,467, U.S. Pat. No. 4,879,231, U.S. Pat. No. 4,882,279, U.S. Pat. No. 4,885,242, U.S. Pat. No. 4,895,800, U.S. Pat. No. 4,929,555, U.S. Pat. No. 5,002,876, U.S. Pat. No. 5,004,688, U.S. Pat. No. 5,032,516, U.S. Pat. No. 5,122,465, U.S. Pat. No. 5,135,868, U.S. Pat. No. 5,166,329, WO 00/56903). In the absence of glucose, *Pichia pastoris* uses methanol as a carbon source which at the same time is a hallmark of a methylotrophic organism. The alcohol oxidase (AOX1) promoter given in SEQ ID NO: 29 controls expression of alcohol oxidase, which catalyses the first step in methanol metabolism. Typically, 30% of the total soluble protein in methanol-induced cells is alcohol oxidase. Several *Pichia* expression vectors carry the AOX1 promoter and use methanol to induce high-level expression of desired heterologous proteins. Expression constructs also integrate into the *Pichia pastoris* genome, creating a transformed and genetically stable host.

Using an expression vector encoding a heterologous pre-protein comprising a signal peptide or a signal peptide with a signal peptidase cleavage site, and a desired protein, methylotrophic yeast strains such as *Pichia pastoris* strains can be manipulated in order to secrete the desired product into the growth medium from where the secreted protein can be purified. It may be advantageous to produce nucleotide sequences encoding the pre-protein possessing a substantially different codon usage. Codons may be selected to increase the rate at which expression of the pre-protein occurs in a particular yeast expression host in accordance with the frequency with which particular codons are utilized by the host. Other reasons for substantially altering the nucleotide sequence encoding the pre-protein, without altering the encoded amino acid sequences, include the production of RNA transcripts having more desirable properties, such as a greater half-life, than transcripts produced from the naturally occurring sequence.

Using a vector comprising the nucleotide sequence encoding the pre-protein that is competent for expression, e.g. operably linked to a promoter or promoter element and to a terminator or terminator element, as well as to sequences required for efficient translation, the host organism is transformed with a vector and transformants are selected. Transformants are then analysed with respect to the yield of recombinant protein secreted into the growth medium. Transformants secreting the highest quantities of enzymatically active recombinant protein are selected. Thus, transformants secreting active bovine pancreatic desoxyribonuclease I with the highest specific activity are selected.

On the one hand, expression yield is dependent on proper targeting of the desired product, e.g. to the secretory pathway by means of a signal peptide such as the α-factor signal peptide from Saccharomyces cerevisiae or the bovine signal peptide of the native bovine pancreatic desoxyribonuclease I pre-protein. On the other hand, expression yield can be increased by increasing the dosage of the gene encoding the desired product, i.e. the copy number of the expression construct in the host organism is amplified. One way to accomplish this is by multiple transformation of an expression vector encoding the desired product. Another way is to introduce the gene encoding the desired product into the host organism using a first and a second expression vector, whereby the second expression vector is based on a selectable marker which differs from the selectable marker used in the first expression vector. The second expression vector encoding the same desired product can even be introduced when the host organism already carries multiple copies of a first expression vector (U.S. Pat. No. 5,324,639; Thill, G. P., et al., Positive and Negative Effects of Multi-Copy Integrated Expression in Pichia pastoris, International Symposium on the Genentics of Microorganisms 2 (1990), pp. 477–490; Vedvick, T., et al., J. Ind. Microbiol. 7 (1991) 197–201; Werten, M. W., et al., Yeast 15 (1999) 1087–1096).

Secretion of expressed bovine pancreatic desoxyribonuclease I into the growth medium directs the mature recombinant protein to the extracytoplasmic space from where it diffuses into growth media. Thus, methylotrophic yeast grown in liquid culture secretes bovine pancreatic desoxyribonuclease I into the liquid growth medium, i.e. the liquid culture medium. This allows a very efficient separation of yeast biomass from the recombinant protein using, e.g. filtration techniques. As a result, bovine pancreatic desoxyribonuclease I purified from this source is very efficiently freed from other enzyme activities such as RNase or protease activities.

High specific enzymatic activity also depends on the structure of bovine pancreatic desoxyribonuclease I. In order to bring about correct structure of a eukaryotic protein, processes like protein folding, the formation of intramolecular disulfide bonds or glycosylation can be involved. It is known that methylotrophic yeast as a eukaryotic host organism for recombinant expression is capable of glycosylating heterologous proteins. It is presumed that recombinant bovine pancreatic desoxyribonuclease I secreted by methylotrophic yeast is glycosylated. Furthermore it might well be possible that in addition disulfide bonds are formed in the course of the secretory pathway of the methylotrophic yeast.

It was surprisingly found that when bovine pancreatic desoxyribonuclease I is expressed and secreted by methylotrophic yeast into the growth medium, this leads to a pancreatic protein with desoxyribonuclease activity, whereby the specific desoxyribonuclease activity of the purified pancreatic protein is very high.

Thus, according to the invention, there is provided a method to produce a bovine pancreatic protein with desoxyribonuclease activity, comprising the steps of (a) providing a vector comprising a nucleotide sequence that encodes a pre-protein consisting of the bovine pancreatic protein and a signal peptide, (b) transforming a methylotrophic yeast strain with the vector, (c) cultivating the transformed methylotrophic yeast strain in a growth medium that contains nutrients and methanol, whereby the methylotrophic yeast strain expresses and secretes the bovine pancreatic protein into the growth medium, and (d) purifying the bovine pancreatic protein from the growth medium, whereby the bovine pancreatic protein is bovine pancreatic desoxyribonuclease I, whereby the bovine pancreatic protein has desoxyribonuclease activity, and whereby the bovine pancreatic protein purified in step (d) is characterised by a specific desoxyribonuclease activity of at least 6,000 units per mg of protein.

Thus, there is provided a method to produce a bovine pancreatic protein with a specific desoxyribonuclease activity of at least 6,000 units per mg of protein purified in step (d), comprising the steps of (a) providing a vector comprising a nucleotide sequence that encodes a pre-protein consisting of the bovine pancreatic protein and a signal peptide, (b) transforming a methylotrophic yeast strain with the vector, (c) cultivating the transformed methylotrophic yeast strain in a growth medium that contains nutrients and methanol, whereby the methylotrophic yeast strain expresses and secretes the bovine pancreatic protein into the growth medium, and (d) purifying the bovine pancreatic protein from the growth medium.

The method therefore results in a purified bovine pancreatic protein that is bovine pancreatic desoxyribonuclease I, expressed as a heterologous pre-protein in a methylotrophic yeast strain and secreted as a mature protein into the growth medium. Therefore, in a very preferred embodiment of the invention, the amino acid sequence of the bovine pancreatic protein is SEQ ID NO: 1, that is a nucleotide sequence comprising preferred codons of methylotrophic yeast.

Yeast-derived as well as non-yeast-derived eukaryotic signal peptides other than those particularly mentioned can be used for the same purpose. Although the signal peptides might not be cleavable by the signal peptidase, a signal peptidase cleavage peptide can be inserted into the pre-protein amino acid sequence, that is between the amino acid sequence of the signal peptide and the amino acid sequence of the bovine pancreatic desoxyribonuclease I polypeptide. Therefore, in yet another very preferred embodiment of the invention, the signal peptide contains a signal peptidase cleavage site which is located directly adjacent to the first amino acid of the bovine pancreatic protein.

Very preferred signal peptides are the signal peptides of the pre-proteins in SEQ ID NO: 2, SEQ ID NO: 3, or SEQ ID NO: 4. Therefore, in another very preferred embodiment of the invention, the amino acid sequence of the expressed pre-protein is selected from the group consisting of (a) SEQ ID NO: 2, (b) SEQ ID NO: 3, and (c) SEQ ID NO: 4. Thus, the vector encodes the amino acid sequences for bovine pancreatic desoxyribonuclease I pre-proteins that enter the secretory pathway when expressed in methylotrophic yeast and particularly in Pichia pastoris.

Translation efficiency of a heterologous protein can be improved by adapting the codons of the nucleotide sequence encoding the heterologous protein according to the preferred codons in the host organism. In yet another very preferred embodiment of the invention, the nucleotide sequence encoding the bovine pancreatic protein is SEQ ID NO: 5. Thus, the nucleotide sequence in SEQ ID NO: 5 consists of codons that are preferred in methylotrophic yeast, particularly in *Pichia*, yet more particularly in *Pichia pastoris*.

In a preferred embodiment of the invention, the nucleotide sequence encoding the pre-protein consists of the nucleotide sequence encoding the signal peptide fused to the nucleotide sequence encoding the bovine pancreatic protein. In a very preferred embodiment of the invention, the nucleotide sequence encoding the signal peptide is selected from the group consisting of (a) SEQ ID NO: 6, (b) SEQ ID NO: 7, and (c) SEQ ID NO: 8. SEQ ID NO: 6 is the nucleotide sequence encoding the amino acid sequence of the signal peptide of the native bovine pancreatic DNase I pre-protein. SEQ ID NO: 7 is the nucleotide sequence encoding the amino acid sequence of the signal peptide of the native bovine pancreatic DNase I pre-protein and an additional signal peptidase cleavage site. SEQ ID NO: 8 is the nucleotide sequence encoding the amino acid sequence of the signal peptide of the α-factor from *Saccharomyces cerevisiae*. This signal peptide is a bipartite signal peptide. Therefore, in yet another very preferred embodiment of the invention, the nucleotide sequence encodes a pre-protein selected from the group consisting of (a) SEQ ID NO: 2, (b) SEQ ID NO: 3, and (c) SEQ ID NO: 4. Moreover, many sources of signal peptides are well known to those skilled in the art. In general, the nucleotide sequence encoding the pre-protein N-terminus of essentially any secreted protein is a potential preferred nucleotide sequence encoding the signal peptide of the bovine pancreatic desoxyribonuclease I pre-protein of the present invention.

In yet a further preferred embodiment of the invention, the nucleotide sequence encoding the pre-protein is operably linked to a promoter or promoter element.

It is also preferred that the promoter or the promoter element stimulates in the methylotrophic yeast strain transcription of the nucleotide sequence that encodes the pre-protein, to which the promoter or the promoter element is operably linked. Very preferred is a promoter or promoter element from *Pichia pastoris*, even more preferred is the *Pichia pastoris* AOX1 promoter given in SEQ ID NO: 29. It is also preferred that in addition the nucleotide sequence that encodes the pre-protein is operably linked with a terminator sequence that directs termination of transcription in the methylotrophic yeast strain. Very preferred is a terminator from *Pichia pastoris*, even more preferred is the *Pichia pastoris* AOX1 terminator.

In yet a further preferred embodiment of the invention, the vector is a plasmid capable of being replicated as an episome in the methylotrophic yeast strain. Thus, the preferred plasmid is a circular nucleic acid molecule that comprises an origin of replication directing replication of the episome in the methylotrophic yeast strain. Moreover, the plasmid comprises a selectable marker that is expressed in the methylotrophic yeast strain, whereby the selectable marker allows to select for the presence of the plasmid in the methylotrophic yeast strain. A very preferred selectable marker is a Zeocin™ resistance gene, that is the native form or a genetically engineered variant of the Sh ble gene from *Streptoalloteichus hindustanus* (Drocourt, D., et al., Nucleic Acids Res. 18 (1990) 4009; Carmels, T., et al., Curr. Genet. 20 (1991) 309–314). Another very preferred selectable marker confers resistance against aminoglycoside antibiotics such as Hygromycin and G418 (Southern, P. J., and Berg, P., J. Mol. Appl. Genet. 1 (1982) 327–341). An example for such a selectable marker is an aminoglycoside phosphotransferase gene.

In yet a further preferred embodiment of the invention, an artificial chromosome capable of being replicated in the methylotrophic yeast strain contains the vector. Thus, the preferred artificial chromosome is a linear nucleic acid molecule that comprises at least one origin of replication, a centromere and terminal telomeres, thereby controlling replication, integrity and mitotic/meiotic distribution of the artificial chromosome in the methylotrophic yeast strain. Moreover, the vector that is contained in the artificial chromosome comprises a selectable marker that is expressed in the methylotrophic yeast strain and that allows to select for the presence of the vector in the artificial chromosome that is replicated in the methylotrophic yeast strain. A very preferred selectable marker is a Zeocin™ resistance gene, that is the native form or an artificial variant of the Sh ble gene from *Streptoalloteichus hindustanus*. Another very preferred selectable marker confers resistance against aminoglycoside antibiotics such as Hygromycin and G418. An example for such a selectable marker is an aminoglycoside phosphotransferase gene.

In yet a further preferred embodiment of the invention, a chromosome of the methylotrophic yeast strain contains the vector. It is very preferred that the vector has a nucleotide sequence identical to a chromosomal sequence, thus allowing integration of the vector into the host chromosome by site-specific recombination. To this end, the *Pichia pastoris* AOX1 locus is even more preferred as a locus for integration the host chromosome by site-specific recombination. It is also very preferred that, the vector comprises a selectable marker that is expressed in the methylotrophic yeast strain and that allows to select for the presence of the vector in the methylotrophic yeast strain. A very preferred selectable marker is a Zeocin™ resistance gene, that is the native form or an artificial variant of the Sh ble gene from *Streptoalloteichus hindustanus*. Another very preferred selectable marker confers resistance against aminoglycoside antibiotics such as Hygromycin and G418. An example for such a selectable marker is an aminoglycoside phosphotransferase gene.

The person skilled in the art is aware of the fact that the yield of secreted bovine pancreatic protein obtainable from growth medium, such as liquid growth medium, can be increased when the number of copies of the nucleotide sequence encoding the pre-protein from which the bovine pancreatic protein is expressed and secreted is increased. Thus, the yield of secreted bovine pancreatic protein obtainable from growth medium can be increased when number of copies of the vector in the genome of the methylotrophic yeast strain is increased. For example, the copy number of the vector can be increased by subjecting the methylotrophic yeast strain to repeated transformations of the vector and repeated selection rounds using increasing concentrations of the selective agent against which the selective marker comprised in the vector confers resistance (U.S. Pat. No. 5,324, 639; Thill, G. P., et al., Positive and Negative Effects of Multi-Copy Integrated Expression in *Pichia pastoris*, International Symposium on the Genentics of Microorganisms 2 (1990), pp. 477–490; Vedvick, T., et al., J. Ind. Microbiol. 7 (1991) 197–201).

The person skilled in the art is also aware of the fact that repeated transformations can be carried out using more than one vector. For example, repeated transformations can be carried out using a first and a second vector, whereby the first and the second vector encode the same pre-protein, whereby in the first and in the second vector the nucleotide sequence encoding the pre-protein is operably linked to a promoter or promoter element, whereby the same bovine pancreatic protein is expressed and secreted, and whereby the first and the second vector confer resistance to a first and a second selection marker.

An example for a first selective marker is the Sh ble gene, that is the Zeocin™ resistance gene (Drocourt, D., et al., Nucleic Acids Res. 18 (1990) 4009; Carmels, T., et al., Curr. Genet. 20 (1991) 309–314). The protein encoded by the Sh ble gene binds Zeocin™ stoichiometrically and with a strong affinity. The binding of Zeocin™ inhibits its toxic activity thereby selecting for transformants containing the Sh ble gene. It is known to a person skilled in the art that increasing the concentration of Zeocin™ as the selective agent in the medium selects for an increase in the number of copies of the vector expressing the Sh ble gene. It is therefore advantageous to use a vector with the Sh ble gene as a selectable marker to generate by repeated transformation multiple transformants of the methylotrophic yeast strain containing multiple copies of the vector. It is furthermore advantageous that transformations are repeated and selection for even more resistant transformants is repeated until for the transformed methylotrophic yeast strain no further increase of the level of resistance to Zeocin™ is obtained anymore or no further increase of the Zeocin™ concentration in the selection medium is possible anymore.

In case a first and a second vector are used, an example for a second selection marker is resistance against aminoglycoside antibiotics (Southern, P. J., and Berg, P., J. Mol. Appl. Genet. 1 (1982) 327–341) such as G418. Thus, an exemplarily second vector expresses a resistance gene that confers resistance against G418. For example, there are several aminoglycoside phosphotransferases known to the art that confer resistance to aminoglycoside antibiotics (van Treeck, U., et al., Antimicrob Agents Chemother. 19 (1981) 371–380; Beck, E., et al., Gene 19 (1982) 327–336). The aminoglycoside phosphotransferase I (APH-I) enzyme has the ability to inactivate the antibiotic G418 and is an established selectable marker in yeast (Chen, X. J., and Fukuhara, H., Gene (1988) 181–192).

Thus, for the purpose of further increasing the dosage of the nucleotide sequence encoding the pre-protein from which the bovine pancreatic protein is expressed and secreted, the second vector is advantageously used for further rounds of transformation and selection, whereby in this case a preferred selective agent is G418 and whereby for transformation the methylotrophic yeast strain transformed with the first vector is used.

In yet a further preferred embodiment of the invention, the methylotrophic yeast strain is a Hansenula, Pichia, Candida or Torulopsis species. In a very preferred embodiment of the invention, the methylotrophic yeast strain is selected from the group consisting of Pichia pastoris, Hansenula polymorpha, Candida boidinii and Torulopsis glabrata.

Even more preferred Pichia pastoris strains are deposited at the American Type Culture Collection (ATCC) with the accession numbers 201178, 201949, 204162, 204163, 204164, 204165, 204414, 204415, 204416, 204417, 20864, 28485, 34614, 60372, 66390, 66391, 66392, 66393, 66394, 66395, 76273, 76274, and 90925.

Yet, an even more preferred methylotrophic yeast strain is the Pichia pastoris strain with the American Type Culture Collection accesssion number 76273 or a derivative thereof.

Even more preferred Hansenula polymorpha strains are deposited at the American Type Culture Collection with the accession numbers 14754, 200499, 200500, 200501, 200502, 200503, 200504, 200505, 200506, 200507, 200508, 200509, 200510, 200511, 200512, 200513, 200838, 200839, 201322, 204205, 22023, 26012, 34438, 36669, 38626, 44954, 44955, 46059, 48180, 58401, 62809, 64209, 66057, 76722, 76723, 76760, 90438, 96694, 96695, MYA-335, MYA-336, MYA-337, MYA-338, MYA-339, and MYA-340.

Even more preferred Candida boidinii strains are deposited at the American Type Culture Collection with the accession numbers 18810, 201209, 20432, 26175, 32195, 32929, 36351, 38256, 38257, 44637, 46498, 48180, 56294, 56507, 56897, 60364, 62807, 90439, 90441, 96315, and 96926.

Even more preferred Torulopsis glabrata strains are deposited at the American Type Culture Collection with the accession numbers 15126, 15545, 2001, 22019, 26512, 28226, 28290, 32312, 32554, 32936, 34147, 34449, 36909, 38326, 4135, 46433, 48435, 58561, 66032, 750, and 90030.

A person skilled in the art is familiar with the purification of bovine pancreatic desoxyribonuclease I by means of chromatography (Funakoshi, A., et al., J. Biochem. (Tokyo) 88 (1980) 1113–1138; Paudel, H. K., and Liao, T. H., J. Biol Chem. 261 (1986) 16006–16011; Nefsky, B., and Bretscher, A., Eur. J. Biochem. 179 (1989) 215–219). It is preferred, however, that bovine pancreatic desoxyribonuclease I which has been secreted by a transformed methylotrophic yeast strain into the growth medium is purified using ion exchange chromatography. Very preferred as a solid phase for ion exchange chromatography is a cation exchanger. In a preferred embodiment of the invention, Bovine pancreatic desoxyribonuclease I binds to the cation exchanger in the presence of a bivalent cation and acetate at low conductivity of the liquid phase, that is in a binding buffer of low conductivity. A preferred bivalent cation is $Mg^{2+}$, $Ca^{2+}$, or $Mn^{2+}$. Preferred for low conductivity is the range of 0.5–10 mS/cm. Very preferred for low conductivity is the range of 1–5 mS/cm. Even more preferred for low conductivity is the range of 2–3 mS/cm. It is also preferred that the binding buffer comprises a protease inhibitor. Furthermore, it is preferred that the binding buffer has an acidic pH. A preferred pH is in the range between 4.5 and 6.9. Even more preferred is a pH of 5.0. Other proteins can be removed almost completely by washing the solid phase repeatedly with the binding buffer of low conductivity, whereby bovine pancreatic desoxyribonuclease I remains bound to the solid phase, that is the cation exchanger. In another preferred embodiment of the invention, elution of bovine pancreatic desoxyribonuclease I is accomplished using an elution buffer with high conductivity in the presence of a bivalent cation and acetate, whereby a small elution volume is advantageous. A preferred bivalent cation is $Mg^{2+}$, $Ca^{2+}$, or $Mn^{2+}$. Also preferred is a concentration of 0.3 M NaCl in the elution buffer. It is furthermore preferred that the elution buffer comprises a protease inhibitor. Furthermore, it is preferred that the elution buffer has an acidic pH. A preferred pH is in the range between 4.5 and 6.9. Even more preferred is a pH of 5.0. Preferred for high conductivity is the range of 10–60 mS/cm. Very preferred for high conductivity is the range of 20–50 mS/cm. Even more preferred for high conductivity is the range of 30–40 mS/cm. It is further preferred to repeat the washing of the solid phase with binding buffer, that is a buffer with low conductivity as described above, in order to achieve a purity higher than about 95% of the eluted bovine pancreatic desoxyribonuclease I. Purity is to be tested by means of SDS PAGE, whereby gels are stained using Coomassie Blue. Also very preferred is a further purification step consisting of affinity chromatography using heparin sepharose. Using this further step, a person skilled in the art is able to achieve about 98% purity of bovine pancreatic desoxyribonuclease I, to be tested by means of SDS PAGE, whereby gels are stained using Coomassie Blue. The specific desoxyribonuclease activity of the affinity-purified bovine pancreatic protein is at least 6,000 units per mg of protein.

Yet another preferred embodiment of the invention is a Pichia pastoris strain with a chromosome that contains a vector comprising a nucleotide sequence that encodes a pre-protein consisting of the bovine pancreatic protein and a signal peptide, operably linked with the Pichia pastoris AOX1 promoter according to SEQ ID NO: 29 or a promoter element thereof, whereby the nucleotide sequence that encodes the pre-protein is SEQ ID NO: 7 or SEQ ID NO: 8, fused to SEQ ID NO:5.

Yet another preferred embodiment of the invention is a bovine pancreatic protein with a specific desoxyribonuclease I activity of at least 6,000 units per mg of protein, obtainable by the method comprising the steps of (a) providing a vector comprising a nucleotide sequence that encodes a pre-protein consisting of the bovine pancreatic protein and a signal peptide, (b) transforming a methylotrophic yeast strain with the vector, (c) cultivating the transformed methylotrophic yeast strain in a growth medium that contains nutrients and methanol, whereby the methylotrophic yeast strain expresses and secretes the bovine pancreatic protein into the growth medium, and (d) purifying the bovine pancreatic protein from the growth medium, whereby the bovine pancreatic protein is bovine pancreatic desoxyribonuclease I, and whereby the bovine pancreatic protein has desoxyribonuclease activity.

Another very preferred embodiment of the invention is a bovine pancreatic protein with a specific desoxyribonuclease activity of at least 6,000 units per mg of protein that retains at least 50% of its specific desoxyribonuclease activity after heat incubation at 75° C. for 60 min, whereby during heat incubation the bovine pancreatic protein is dissolved in a storage buffer containing 20 mM TrisHCl, 2 mM $MgCl_2$, 4 mM $CaCl_2$, 50% glycerol, pH 7.6.

Yet another preferred embodiment of the invention is the use of a bovine pancreatic protein with a specific desoxyribonuclease activity of at least 6,000 units per mg of protein for hydrolysing DNA.

Yet another preferred embodiment of the invention is a kit of parts containing a bovine pancreatic protein with a specific desoxyribonuclease activity of at least 6,000 units per mg of protein and a reaction buffer comprising a divalent cation. Yet another very preferred embodiment of the invention is the kit of parts, whereby the bovine pancreatic protein is dissolved in a storage buffer containing water, glycerol, a protease inhibitor, and a divalent cation, whereby the reaction buffer contains a divalent cation contains selected from the group consisting of $Mg^{2+}$, $Ca^{2+}$ and $Mn^{2+}$.

The method of the present invention presents an alternative to the purification of bovine pancreatic desoxyribonuclease I. Furthermore, it allows the production and purification of an active bovine pancreatic desoxyribonuclease I enzyme with a very high specific activity.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Figure 1:
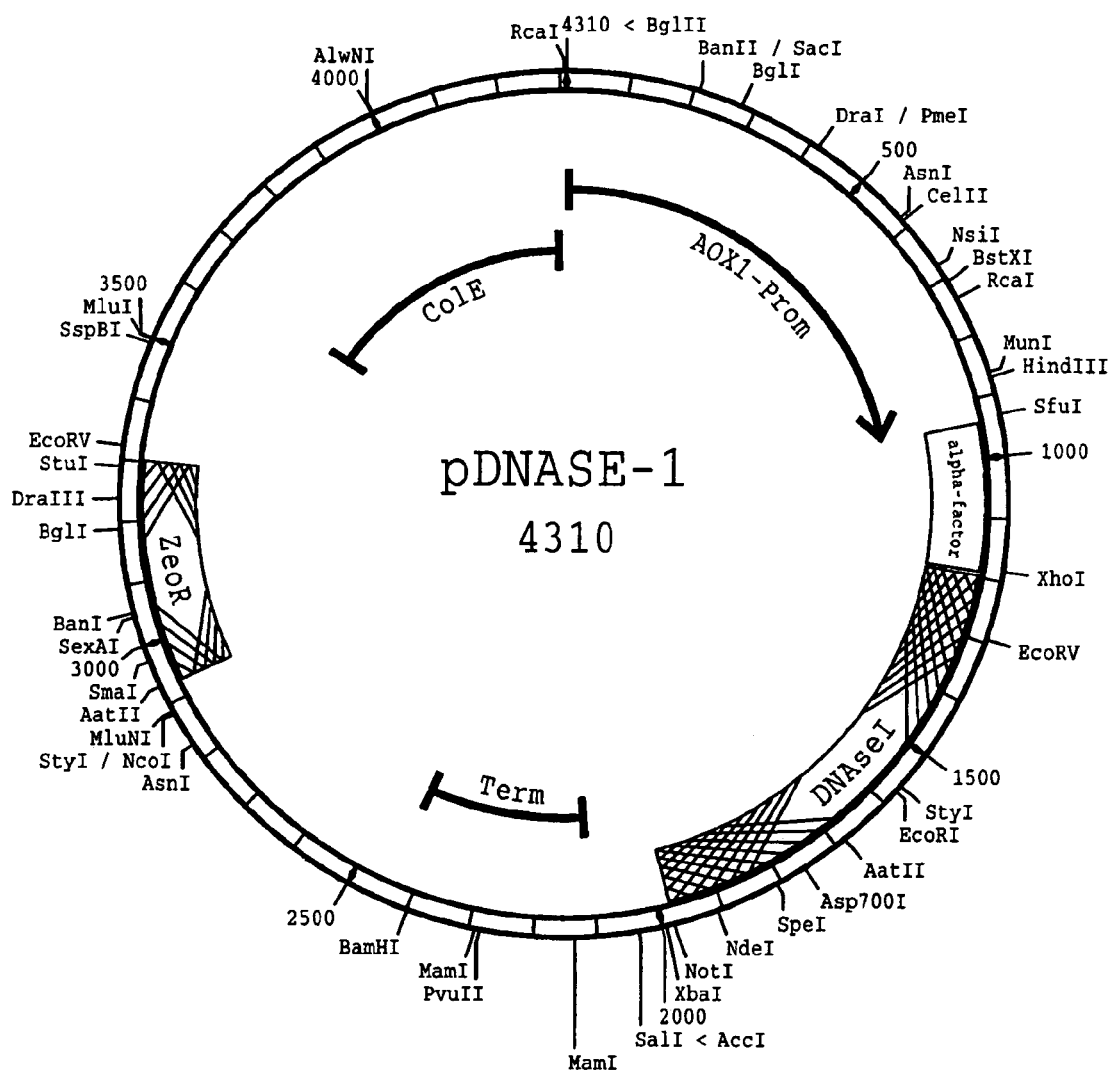
FIG. 1 Map of the plasmid pDNASE-1 which is a derivative of the commercially available plasmid pPICZαA (Invitrogen) that confers resistance to Zeocin™. The insert denoted "DNAseI" is the synthetic DNA sequence encoding the mature bovine secreted desoxyribonuclease I protein (SEQ ID NO: 5) that is fused to the nucleotide sequence encoding the α-factor signal peptide from Saccharomyces cerevisiae (SEQ ID NO: 8). "AOX1-Prom" denotes the Pichia pastoris AOX1 promoter, "Term" denotes the Pichia pastoris AOX1 terminator.
Figure 2:
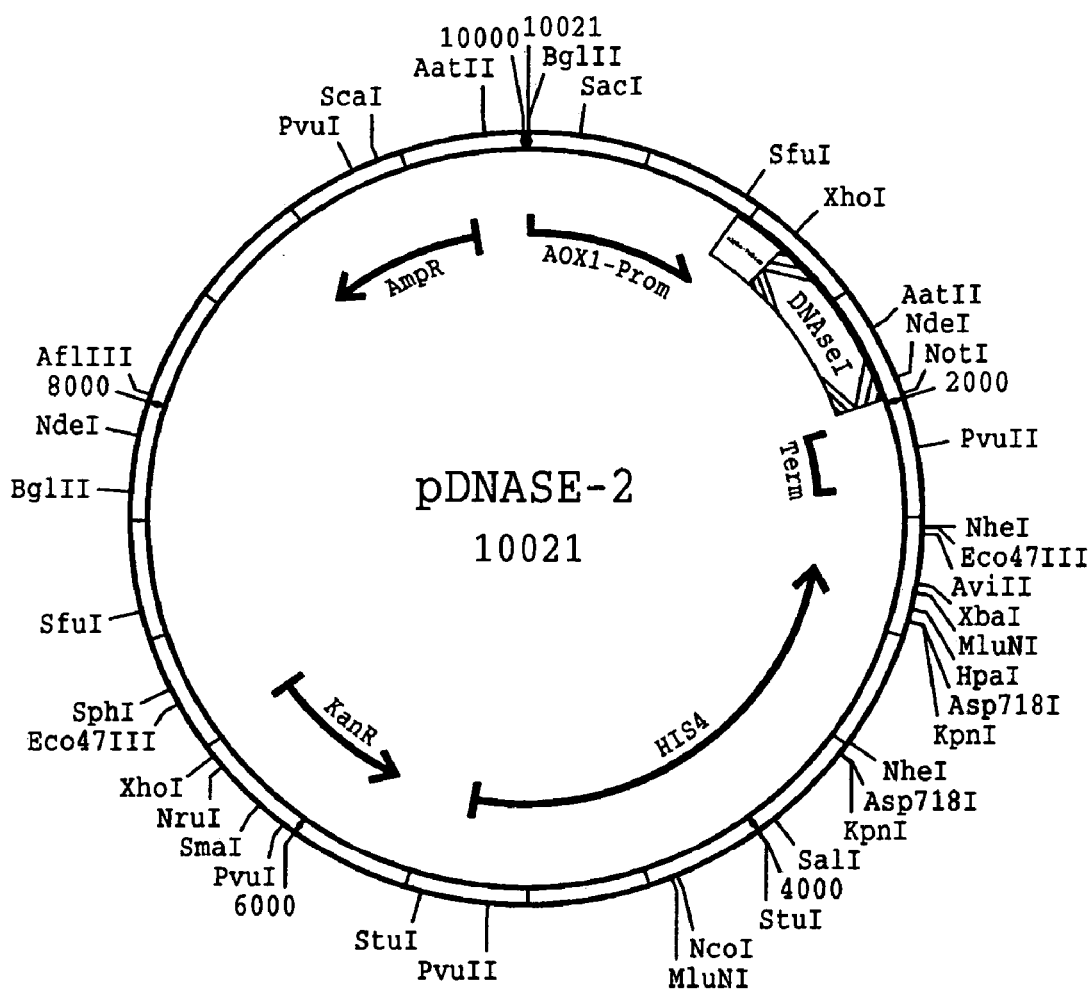
FIG. 2 Map of the plasmid pDNASE-2 which is a derivative of the commercially available plasmid pPIC9K (Invitrogen) that confers resistance to G418. The insert denoted "DNAseI" is the synthetic DNA sequence encoding the mature bovine secreted desoxyribonuclease I protein (SEQ ID NO: 5) that is fused to the nucleotide sequence encoding the α-factor signal peptide from Saccharomyces cerevisiae (SEQ ID NO: 8). "AOX1-Prom" denotes the Pichia pastoris AOX1 promoter, "Term" denotes the Pichia pastoris AOX1 terminator.
Figure 3:
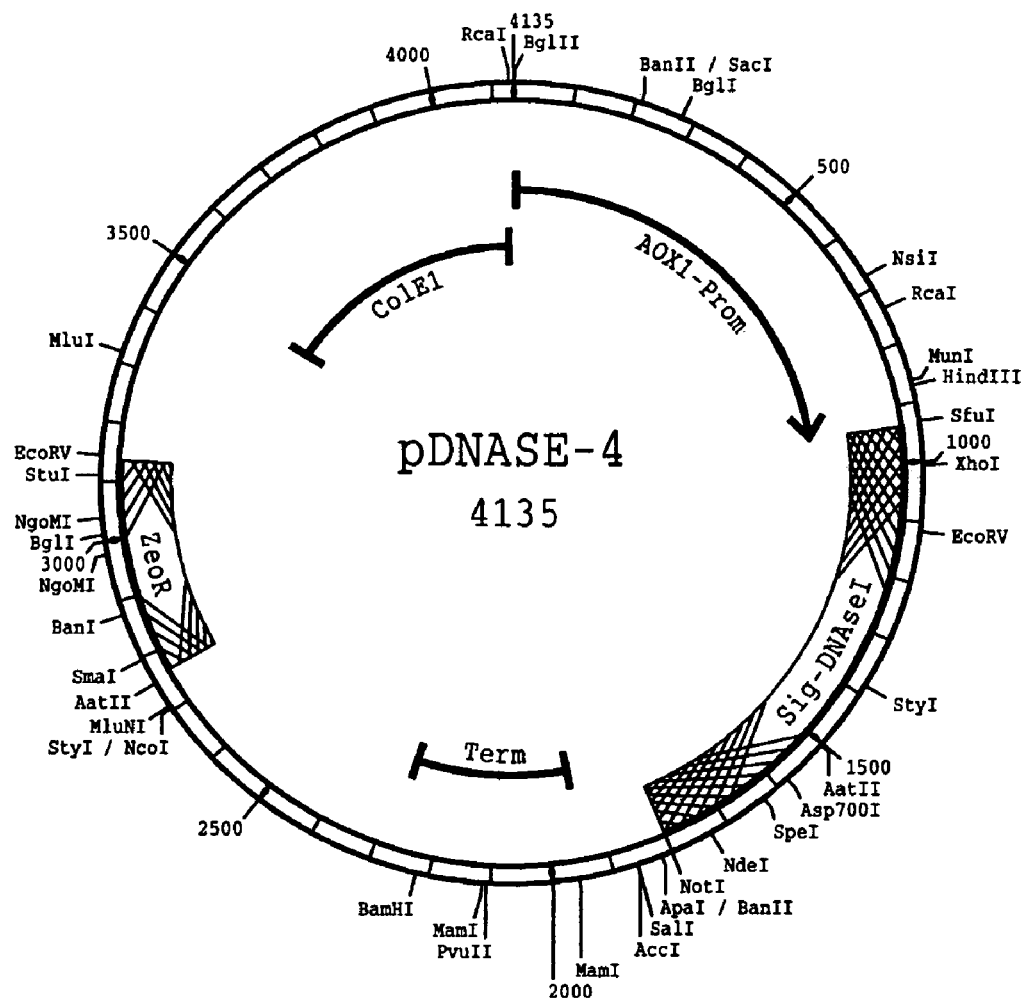
FIG. 3 Map of the plasmid pDNASE-4 which is a derivative of the commercially available plasmid pPICZαA (Invitrogen) that confers resistance to Zeocin™. The insert denoted "Sig-DNAseI" is the fusion of the synthetic DNA sequence encoding the mature bovine secreted desoxyribonuclease I protein (SEQ ID NO: 5) with the nucleotide sequence encoding the native bovine pancreatic desoxyribonuclease I signal peptide sequence and an additional signal peptidase cleavage site (SEQ ID NO: 7). "AOX1-Prom" denotes the Pichia pastoris AOX1 promoter, "Term" denotes the Pichia pastoris AOX1 terminator.
Figure 4:
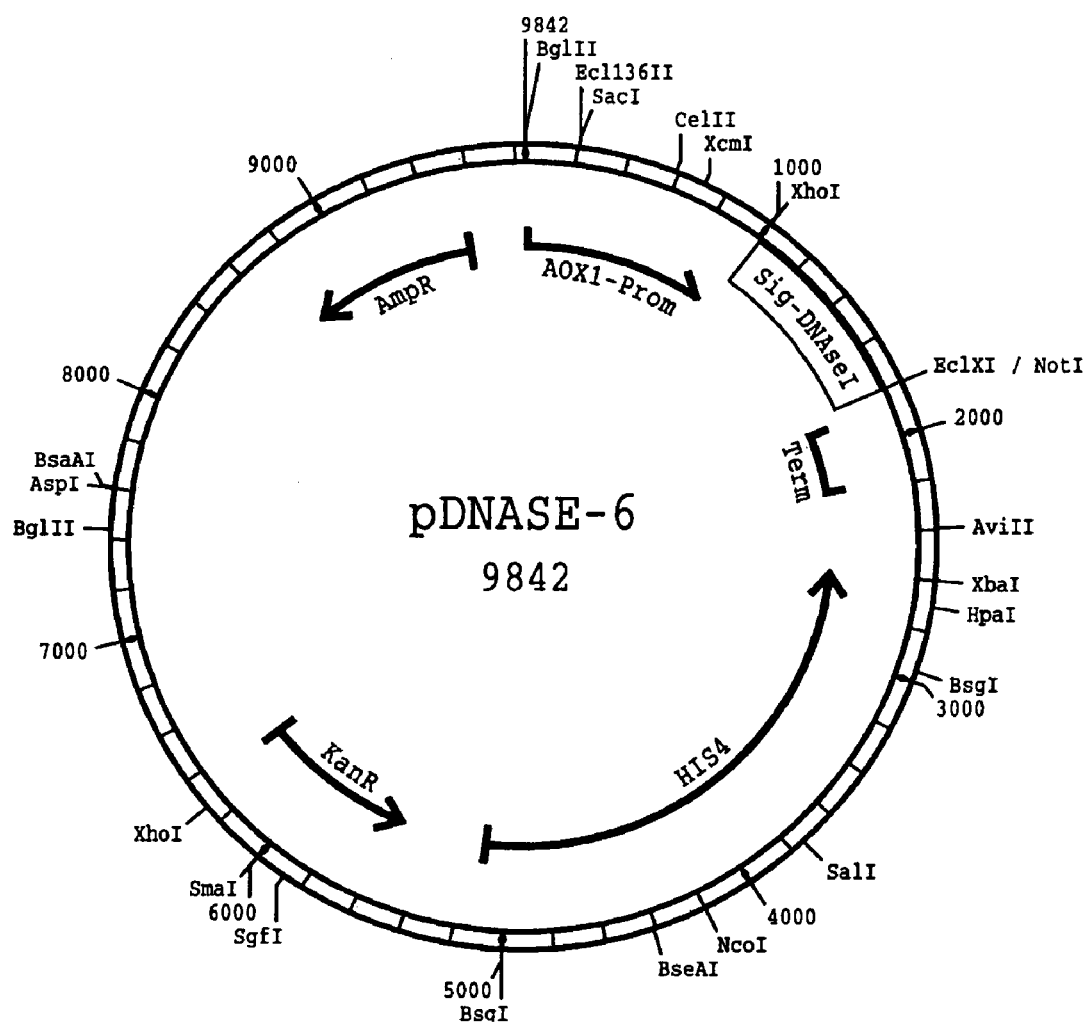
FIG. 4 Map of the plasmid pDNASE-6 which is a derivative of the commercially available plasmid pPIC9K (Invitrogen) that confers resistance to G418. The insert denoted "Sig-DNAseI" is the fusion of the synthetic DNA sequence encoding the mature bovine secreted desoxyribonuclease I protein (SEQ ID NO: 5) with the nucleotide sequence encoding the native bovine pancreatic desoxyribonuclease I signal peptide sequence and an additional signal peptidase cleavage site (SEQ ID NO: 7). "AOX1-Prom" denotes the Pichia pastoris AOX1 promoter, "Term" denotes the Pichia pastoris AOX1 terminator.

Synthesis of a Yeast-Adapted Nucleotide Sequence Encoding the Mature Bovine Pancreatic Desoxyribonudease I Protein Generally, standard methods of molecular biology were applied as described in Sambrook, Fritsch & Maniatis, Molecular Cloning, A Laboratory Manual, 3rd edition, CSHL Press, 2001.

In order to optimise each codon for the use in yeast, the encoding vector was synthesised de novo. The sequence of the mature bovine pancreatic desoxyribonuclease I protein is given in SEQ ID NO: 1 and consists of 260 amino acids. Back-translation resulted in a nucleotide sequence of 783 base pairs including a stop codon. The yeast-adapted coding sequence is given in SEQ ID NO: 5. The coding sequence was divided into 18 DNA oligonucleotides having a length of between 42 and 72 nucleotides. The single-stranded DNA oligonucleotides were designed as a series of alternating coding strand and non-coding strand fragments, having complementary 5' and 3' overlaps with the neighbouring fragments. The DNA oligonucleotides used in this manner are given in SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26. The overlapping region was chosen such that unspecific binding during an annealing reaction was largely suppressed. The DNA oligonucleotides representing the 5' end and 3' end of the sequence encoding SEQ ID NO: 1 included restriction endonuclease cleavage sites located upstream and downstream of the coding sequence, in order to facilitate insertion of the artificial nucleotide sequence into expression vectors. Upstream the 5' end of the sequence encoding SEQ ID NO: 1, an Xho I cleavage site and the codons for two amino acids of the C-terminus of the α-factor signal peptide from *Saccharomyces cerevisiae* were added. Downstream of the stop codon, i.e. the 3' end of the sequence encoding SEQ ID NO: 1, Not I and Bgl II cleavage sites were added.

Three larger DNA fragments were synthesised separately from DNA oligonucleotides by means of the polymerase chain reaction (PCR). The first reaction comprised the DNA oligonucleotides given in SEQ ID NO: 9, SEQ ID NO: 10, SEQ ID NO: 11, SEQ ID NO: 12, SEQ ID NO: 13, and SEQ ID NO: 14. The second reaction comprised the DNA oligonucleotides given in SEQ ID NO: 15, SEQ ID NO: 16, SEQ ID NO: 17, SEQ ID NO: 18, SEQ ID NO: 19, and SEQ ID NO: 20. The third reaction comprised the DNA oligonucleotides given in SEQ ID NO: 21, SEQ ID NO: 22, SEQ ID NO: 23, SEQ ID NO: 24, SEQ ID NO: 25, and SEQ ID NO: 26. In the course of PCR, in each cycle overlapping termini were annealed and complementary DNA strands were synthesised. Therefore, the DNA oligonucleotides were enlarged stepwise until the final length of the fragment was reached. To this end, the annealing temperature was chosen according to the requirements of the overlapping regions, i.e. the region with the lowest melting temperature determined the annealing temperature. During subsequent cycles, the final fragment was amplified.

By means of agarose gel electrophoresis the three larger DNA fragments were separated from any by-products. Gel bands corresponding to the desired fragments were excised and DNA was isolated from agarose blocks using the "QIAquick Gel Extraction Kit" (Qiagen catalogue no. 28704). The three larger DNA fragments were then combined in a further PCR in the same fashion as described above, in order to synthesise the complete vector encoding the mature bovine pancreatic desoxyribonuclease I protein. The first five PCR cycles were made with the three larger DNA fragments without any further primers added. Again, the annealing temperature was chosen according to the requirements of the overlapping regions, i.e. the region with the lowest melting temperature. Subsequently, two DNA oligonucleotides representing the termini of the complete artificial nucleotide sequence were added. The annealing temperature was raised according to the requirements of the added primers, i.e. the primer with the lowest melting temperature determines the annealing temperature. The complete artificial nucleotide sequence was amplified in the course of 25 PCR cycles.

The complete DNA fragment encoding the mature bovine pancreatic desoxyribonuclease I protein was subsequently inserted into a cloning vector and propagated in *E. coli* using conventional techniques (Sambrook, Fritsch & Maniatis, Molecular Cloning, A Laboratory Manual, 3rd edition, CSHL Press, 2001). The nucleotide sequence of the complete DNA fragment was verified by sequencing.

EXAMPLE 2

Cloning of the Nucleotide Sequence Encoding the Bovine Signal Peptide of the Native Bovine Pancreatic Desoxyribonuclease I Pre-protein Generally, the methods suggested and described in the Invitrogen manuals "*Pichia* Expression Kit" Version M 011102 25–0043, "pPICZ A, B, and C" Version D 110801 25–0148, "pPICZα A, B, and C" Version E 010302 25–0150, and "pPIC9K" Version E 030402 25–0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

In order to provide a nucleotide sequence encoding the bovine signal peptide of the native bovine pancreatic desoxyribonuclease I pre-protein, two complementary single-stranded DNA oligonucleotides were synthesised. As in Example 1, the codons were designed according to the preferred codon usage in methylotrophic yeast. The DNA oligonucleotides used are given in SEQ ID NO: 27, SEQ ID NO: 28. The 5' ends of the DNA oligonucleotides were designed such that the annealed, i.e. double-stranded nucleic acid would have terminal overhangs identical to the overhangs which would have been created by cleavage of restriction endonucleases Sfu I and Xho I. The orientation of the overhangs is given with respect to the coding strand with the Sfu I site being located at its 5' end and the Xho I site being located at its 3' end. Upstream of the coding sequence an optimal Kosak-sequence has been inserted, to facilitate efficient initiation of translation in the host organism.

Of each of the two DNA oligonucleotides 5 μg were dissolved in 10 mM TrisHCl pH 7.5, 10 mM MgCl$_2$, 50 mM NaCl, 1 mM Dithiothreitol and heated at 100° C. for 5 minutes, so that unwanted secondary structures and irregular hybridisation products were broken up. Subsequently, hybridisation was allowed to take place by slowly cooling the mixture to room temperature. The double-stranded nucleic acid was analysed in an agarose gel and directly used in a ligation reaction with the expression vector pPICZA (Invitrogen, Carlsbad, Calif., USA) which was linearised before with Sfu I and Xho I. The resulting vector which carried the nucleotide sequence encoding the bovine signal peptide of the native bovine pancreatic desoxyribonuclease I pre-protein was subsequently analysed by restriction enzyme digestion and agarose gel electrophoresis as well as by sequencing.

EXAMPLE 3

Cloning of the Artificial Vector Encoding Mature Bovine Pancreatic Desoxyribonuclease I in Various Expression Vectors Generally, the methods suggested and described in the Invitrogen manuals "*Pichia* Expression Kit" Version M 011102 25–0043, "pPICZ A, B, and C" Version D 110801 25–0148, "pPICZα A, B, and C" Version E 010302 25–0150, and "pPIC9K" Version E 030402 25–0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

The artificial DNA fragment encoding the mature bovine pancreatic desoxyribonuclease I that was generated from PCR fragments (see Example 1) was excised with Xho I and Bgl II (Roche Diagnostics GmbH). The fragment was isolated using the "QIAquick Gel Extraction Kit" according to the instructions of the manufacturer.

Case 1: The fragment was ligated into the pPICZA vector fusing the nucleotide sequence encoding the mature bovine pancreatic desoxyribonuclease I to the nucleotide sequence encoding the bovine signal peptide of the native bovine pancreatic desoxyribonuclease I pre-protein (see Example 1). Before the ligation reaction, the vector was similarly cleaved with Xho I and Bgl II, and isolated.

Case 2: The fragment was ligated into the pPICZαA vector fusing the nucleotide sequence encoding the mature bovine pancreatic desoxyribonuclease I to the nucleotide sequence encoding the α-factor signal peptide from *Saccharomyces cerevisiae*. Before the ligation reaction, the vector was similarly cleaved with Xho I and Bgl II, and isolated.

The cloning procedure followed in Case 1 inserted a linker sequence—encoding Leucine-Glutamic acid-Lysine-Arginine—into the reading frame between the bovine signal peptide of the native bovine pancreatic desoxyribonuclease I pre-protein and the sequence encoding the mature protein. The Leucine-Glutamic acid sequence was inserted by virtue of the Xho I site (CTCGAG). The Lysine-Arginine sequence is known to represent a KEX-2 signal peptidase cleavage site, needed to cleave off the signal peptide from the pre-protein in the course of the secretory pathway. The nucleotide sequence for the Lysine-Arginine sequence is comprised in SEQ ID NO: 7 that corresponds to the signal peptide amino acid sequence in SEQ ID NO: 3. The cloning procedure followed in Case 2 inserted the nucleotide sequence encoding the mature bovine pancreatic desoxyribonuclease I directly and in-frame after the nucleotide sequence encoding the α-factor signal peptide from *Saccharomyces cerevisiae*.

In both cases, the nucleotide sequence encoding the recombinant pre-protein were under the control of the *P. pastoris* AOX-1 promoter (SEQ IN NO.: 29) which is inducible by methanol.

Construction was accomplished by joining in a total volume of 10 μl 20 ng of linearised vector fragment (in a volume of 1 μl), 100 ng of PCR fragment (in 3 μl), and incubation overnight at 16° C. in the presence of T4 DNA ligase (Roche Diagnostics GmbH) according to the instructions of the manufacturer. 5 μl of the ligation preparation were subsequently used to transform competent (Hanahan, 1983) *E. coli* XL1Blue cells (Stratagene), in a total volume of 205 μl. Following incubation on ice for 30 min, cells were heat-shocked at 42° C. for 90 sec. Subsequently, cells were transferred into 1 ml LB medium and incubated for 1 h at 37° C. to allow for expression of selection markers. Aliquots were plated afterwards on LB plates containing 100 μg/ml Zeocin and incubated for 15 h at 37° C. Resistant clones were picked, plasmids were isolated (Sambrook, Fritsch & Maniatis, Molecular Cloning, A Laboratory Manual, 3rd edition, CSHL Press, 2001) and tested by means of restriction analysis as well as sequence analysis. Construct clones verified to be free of errors and cloning artifacts were selected. The expression vector harbouring bovine pancreatic desoxyribonuclease I with the α-factor signal peptide from *Saccharomyces cerevisiae* was designated pDNASE-1, the expression vector harbouring bovine pancreatic desoxyribonuclease I with the bovine signal peptide of the native bovine pancreatic desoxyribonuclease I pre-protein was designated pDNASE-4.

EXAMPLE 4

Transformation of *Pichia pastoris* with pDNASE-1 and pDNASE-4

Generally, the methods suggested and described in the Invitrogen manuals "*Pichia* Expression Kit" Version M 011102 25–0043, "pPICZ A, B, and C" Version D 110801 25–0148, "pPICZα A, B, and C" Version E 010302 25–0150, and "pPIC9K" Version E 030402 25–0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

The host strains used were *Pichia pastoris* X-33, GS115, KM71H and SMD1168 (Invitrogen). Preferred strains were X-33 and KM71H. Transformation was aimed at stably integrating expression constructs into the genome of the host organism.

Initially, 5 ml YPD medium (YPD=yeast peptone dextrose; Invitrogen) was inoculated with a *P. pastoris* colony and pre-cultured on a shaker overnight at 30° C. To prepare transformation-competent cells, 100 μl of the pre-culture were added as inoculum to 200 ml of fresh YPD medium and grown until an $OD_{600\ nm}$ of between 1.3 and 1.5 was reached. The cells were centrifuged at 1,500×g for 5 min and resuspended in 200 ml ice cold (0° C.) sterile water. The cells were centrifuged again at 1,500×g for 5 min and resuspended in 100 ml ice cold sterile water. The cells were centrifuged one more time at 1,500×g for 5 min and resuspended in 10 ml ice cold 1 M sorbitol (ICN). The cells prepared in this way were kept on ice and used for transformation immediately.

The expression vectors pDNASE-1 and pDNASE-4 to be used for transformation were linearised using the Sac I restriction endonuclease (Roche Diagnostics GmbH), precipitated and resuspended in water. Transformation was accomplished by electroporation using a "Gene Pulser™" (BioRad). For a transformation setting, 80 μl *P. pastoris* cells in 1 M sorbitol solution were mixed gently with 1 μg of linearised expression vector DNA and transferred into an ice cold cuvette which was then kept on ice for 5 min. Subsequently, the cuvette was transferred into the Gene Pulser. Electroporation parameters were 1 kV, 1 kΩ and 25 μF. Following electroporation, 1 ml 1 M sorbitol solution was added to the cell suspension was subsequently plated onto YPDS plates (YPDS=yeast peptone dextrose sorbitol; Invitrogen) containing 100 μg/ml Zeocin™ (Invitrogen), with 100–150 μl of cell suspension being spread on a single plate. YPDS plates were incubated at 30° C. for 2–4 days. Yeast clones were transferred onto gridded minimal dextrose plates. Colonies from these plates were picked and separately resuspended in sterile water. The cells were digested with 17.5 units of lyticase (Roche Diagnostics GmbH) for 1 h at 30° C. and afterwards frozen for 10 min at –80° C. By means of PCR, the presence of the expression cassettes of pDNASE-1 and pDNASE-4 was verified. The term "expression cassette" denotes a nucleotide sequence encoding the bovine pancreatic desoxyribonuclease I pre-protein, operably linked to the AOX1 promoter and the AOX1 terminator, whereby the expression cassette is derived from the respective pDNASE vector used for transformation. As for vectors containing an expression cassette, the terms "vector" and "expression vector" are synonyms.

Positive clones, i.e. clones that were tested positively for the presence of complete expression cassettes stably integrated into the genome were used for further characterisation of bovine pancreatic desoxyribonuclease I expression.

Additionally, control transformations were made with the recipient *Pichia pastoris* X33 strain using the pPICZαA vector. Positive clones were obtained and verified in a similar fashion.

EXAMPLE 5

Expression and Secretion of Recombinant Bovine Pancreatic Desoxyribonuclease I, Analysis of Pre-proteins with Different Signal Peptides Generally, the methods suggested and described in the Invitrogen manuals "*Pichia* Expression Kit" Version M 011102 25–0043, "pPICZ A, B, and C" Version D 110801 25–0148, "pPICZα A, B, and C" Version E 010302 25–0150, and "pPIC9K" Version E 030402 25–0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

A set of positive clones (usually 20–30) transformed with pDNASE-1 and pDNASE-4 (see Example 4) were grown as shaking cultures overnight, each in 3 ml BMGY medium (BMGY=buffered glycerol-complex medium; Invitrogen). Afterwards, the $OD_{600nm}$ values of the cultures were determined before they were passaged into shaking flasks, each containing 10 ml BMMY medium (Invitrogen) at pH 3. Pre-cultures were used as inoculum to result each in an $OD_{600nm}$ of 1. The cultures were kept on a shaker at 30° C. In parallel, positive control clones were cultured under the same conditions.

BMMY (BMMY buffered methanol-complex medium;) medium comprises methanol (Mallinckrodt Baker B.V.) which is an inductor of the AOX-1 promoter that controls transcription of the recombinant bovine pancreatic desoxyribonuclease I sequences inserted into the expression vectors.

Samples of 500 μl were taken from the shaking flask in 24 h intervals over a total time of 72 h. When a sample aliquot was removed, the culture was also fed with 0.5% methanol. Samples of the supernatant growth medium were tested for desoxyribonuclease enzymatic activity.

EXAMPLE 6

Analysis of Expression of Recombinant Bovine Pancreatic Desoxyribonuclease I

Of the sample aliquots obtained as described in Example 5 firstly the $OD_{600nm}$ was determined. Subsequently the cells were pelleted by centrifugation and the supernatant was saved. Desoxyribonuclease activity was measured in the undiluted supernatant as well as in a 1:10 dilution (Example 11).

While control clones transformed with the pPICZαA vector did not lead to any measurable desoxyribonuclease activity in the medium, *Pichia* strains transformed with both pDNASE-1 and pDNASE-4 showed desoxyribonuclease activity due to bovine pancreatic desoxyribonuclease I secreted into the growth medium, i.e. the culture medium. It could therefore be concluded that that expression of a recombinant pre-protein comprising either the α-factor signal peptide from *Saccharomyces cerevisiae* or the bovine signal peptide of the native bovine pancreatic desoxyribonuclease I pre-protein enables secretion of an active enzyme having desoxyribonuclease activity.

Regarding the yield of secreted mature protein, i.e. the desired bovine pancreatic desoxyribonuclease I, there were no obvious differences between the strains expressing the pre-protein with the bovine signal peptide of the native bovine pancreatic desoxyribonuclease I pre-protein and the pre-protein with the α-factor signal peptide from *Saccharomyces cerevisiae*.

EXAMPLE 7

Increasing Expression Yield By Multiple Transformation and Increased Zeocin™ Concentration Generally, the methods suggested and described in the Invitrogen manuals "*Pichia* Expression Kit" Version M 011102 25–0043, "pPICZ A, B, and C" Version D 110801 25–0148, "pPICZα A, B, and C" Version E 010302 25–0150, and "pPIC9K" Version E 030402 25–0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

The yeast clones transformed with the expression vectors pDNASE-1-and pDNASE-4 that were found to produce the highest desoxyribonuclease activities in supernatant media were subjected to repeated electroporation using the same expression vector as previously. Conditions for electroporation were as described in Example 4 with the exception that YPDS plates contained Zeocin™ at increased concentrations, that is between 1,000 and 2,000 μg/ml. The concentration of the antibiotic was increased in order to select for transformants having incorporated into their genome multiple copies of the respective expression vector. Yeast clones with increased resistance to the antibiotic were transferred onto gridded minimal dextrose plates. As already described in Example 5, pre-cultures were made from individual yeast clones and expression was measured by determining the desoxyribonuclease enzymatic activity secreted into the growth medium as described in Example 6. Individual clones were found that produced an increased amount of desoxyribonuclease activity. This was the case for yeast transformants expressing both types of recombinant pre-protein, i.e. pre-protein comprising either the α-factor signal peptide from *Saccharomyces cerevisiae* or the bovine signal peptide of the native bovine pancreatic desoxyribonuclease I pre-protein. On the average, desoxyribonuclease activity measured in the supernatant of *Pichia* strains repeatedly transformed with pDNASE-1- or pDNASE-4 was between twice to three times as high compared to the respective precursor strains that had undergone only a single transformation.

Regarding the yield of secreted mature protein, there were no obvious differences between the strains expressing the pre-protein with the bovine signal peptide of the native bovine pancreatic desoxyribonuclease I pre-protein and the pre-protein with the α-factor signal peptide from *Saccharomyces cerevisiae*.

EXAMPLE 8

Increasing Expression Yield By Means of Introducing a Different Expression Vector Allowing to Apply Further Selection Pressure Generally, the methods suggested and described in the Invitrogen manuals "*Pichia* Expression Kit" Version M 011102 25–0043, "pPICZ A, B, and C" Version D 110801 25–0148, "pPICZα A, B, and C" Version E 010302 25–0150, and "pPIC9K" Version E 030402 25–0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

From the expression vectors pDNASE-1 and pDNASE-4 the expression cassette consisting of a part of the AOX-1 promoter and the reading frame for the respective pre-protein (see Figure X) was excised using restriction endonucleases Sac I and Xba I (Roche Diagnostics GmbH). The resulting cleavage products were separated by agarose gel electrophoresis. In the case of pDNASE-1, a fragment having the size of 1765 bp was excised and isolated using the "QIAquick Gel Extraction Kit" (Qiagen). In the case of pDNASE-4, a fragment having the size of 1560 bp was excised and isolated using the "QIAquick Gel Extraction Kit" (Qiagen). In both fragments, the Xba I overhang was converted to a blunt end using Klenow polymerase (Roche Diagnostics GmbH).

The vector pPIC9K (Invitrogen) was cleaved using restriction endonucleases Sac I and Not I (Roche Diagnostics GmbH). The resulting cleavage products were separated by agarose gel electrophoresis. A fragment with a size of 8956 bp was excised and isolated using the "QIAquick Gel Extraction Kit" (Qiagen). The Not I overhang was converted to a blunt end using Klenow polymerase (Roche Diagnostics GmbH). The expression cassettes prepared from pDNASE-1 and pDNASE-4 were inserted separately. Ligation, bacterial transformation and cloning procedures were performed as described in Example 3 with the execution that transformed bacterial clones were selected on LB plates containing 100 μg/ml of the antibiotic ampicillin. Clones were verified by means of restriction analysis and sequencing. The pPIC9K-derived expression vector harbouring bovine pancreatic desoxyribonuclease I with the α-factor signal peptide from *Saccharomyces cerevisiae* was designated pDNASE-2, the pPIC9K-derived expression vector harbouring bovine pancreatic desoxyribonuclease I with the bovine signal peptide of the native bovine pancreatic desoxyribonuclease I pre-protein was designated pDNASE-6.

Using the pPIC9K-derived expression vectors, resistance to the antibiotic G418 was introduced. Among the *Pichia pastoris* Zeocin™-resistant transformants having incorporated into their genome multiple copies of the pDNASE-1 and pDNASE-4 expression vectors those were selected that secreted into the growth medium the highest amounts of desoxyribonuclease activity. Clones containing multiple copies of pDNASE-1 were transformed with pDNASE-2 and clones containing multiple copies of pDNASE-4 were transformed with pDNASE6. Expression vectors to be used were linearised using the Sal I restriction endonuclease (Roche Diagnostics GmbH). 1 μg of the respective linearised expression vector was used for transformation which was performed as described in Example 4. Following electroporation, the cells were kept at 4° C. in 1 M sorbitol for a period of between 1 and 3 days, in order to allow the cells become resistant to the antibiotic. The cell suspension was plated onto YPDS plates (Invitrogen) containing 1, 2 and 4 mg/ml G418 (Roche Diagnostics GmbH), with 100–200 μl of cell suspension being spread on a single plate. YPDS plates were incubated at 30° C. for 3–5 days. Yeast clones were transferred onto gridded minimal dextrose plates. Clones originating from YPDS plates with the highest G418 concentration were preferentially transferred. Selected clones were characterised further as described in Example 4.

Multiply transformed and verified *Pichia* clones carrying multiple copies of expression vectors conferring Zeocin™ resistance as well as the expression vector conferring resistance to G418 were characterised with respect to the amount of desoxyribonuclease activity secreted into the growth medium. Assays were performed as described in Example 5. Clones harbouring pDNASE-1 and pDNASE-2 constructs were identified which produced an even higher level of secreted desoxyribonuclease enzymatic activity than the precursor clones containing only multiple copies of pDNASE-1 but not pDNASE-2. Additionally, clones harbouring pDNASE-4 and pDNASE-6 constructs were identified which produced an even higher level of secreted desoxyribonuclease enzymatic activity than the precursor clones containing only multiple copies of pDNASE-4 but not pDNASE-6. On the average, desoxyribonuclease activity measured in the supernatant of cultures that were transformed with pDNASE-2 or pDNASE-6, i.e. in addition to multiple transformations with pDNASE-1 or pDNASE-4, was found to be about four times as high when compared to the respective precursor strains that had undergone only a single transformation.

Regarding the yield of secreted mature protein, there were no obvious differences between the strains expressing the pre-protein comprising the bovine signal peptide of the native bovine pancreatic desoxyribonuclease I pre-protein and the pre-protein comprising the α-factor signal peptide from *Saccharomyces cerevisiae*.

EXAMPLE 9

Purification of Recombinant Bovine Pancreatic Desoxyribonuclease I Protein from Liquid Culture Supernatant Biomass was removed from the supernatant growth medium by filtration or by centrifugation. Bovine pancreatic desoxyribonuclease I was subsequently purified by means of ion exchange chromatography using a cation exchanger. A cation exchanger that was used with success was SP sepharose. Bovine pancreatic desoxyribonuclease I was bound to the cation exchanger at low conductivity of the liquid phase, that is in a binding buffer of low conductivity. Low conductivity corresponded to a value of conductivity between 2–3 mS/cm. The binding buffer had a pH of 5.0 and contained 20 mM $Ca^{2+}$ acetate and 1 mM Pefabloc™. Other proteins were removed by washing the solid phase repeatedly with binding buffer, whereby the bovine pancreatic desoxyribonuclease I remained bound by the solid phase, that is the cation exchanger. Elution of bovine pancreatic desoxyribonuclease I was accomplished using an elution buffer with high conductivity. High conductivity corresponded to a value of conductivity between 30–40 mS/cm. The elution buffer had a pH of 5.0 and contained 0.3 M NaCl, 20 mM $Ca^{2+}$ acetate and 1 mM Pefabloc™. The purity of the bovine pancreatic desoxyribonuclease I achieved after this step was higher than about 95% as tested by means of SDS PAGE, whereby gels were stained using Coomassie Blue. The subsequent purification step was affinity chromatography using heparin sepharose to remove RNase activity. The buffer system used was 2 mM Tris/HCl pH 6.5 with a conductivity 2.1+/−0.1 mS/cm. The bovine pancreatic desoxyribonuclease I not is bound to the solid phase. Following this step, the purity of the bovine pancreatic desoxyribonuclease I was higher than about 98% as tested by means of SDS PAGE, whereby gels were stained using Coomassie Blue. The specific desoxyribonuclease activity of the affinity-purified bovine pancreatic desoxyribonuclease I was higher than or equal to 6,000 units per mg of protein.

EXAMPLE 10

Assay to Determine the Specific Desoxyribonuclease Activity of Purified Bovine Pancreatic Desoxyribonuclease I In Growth Culture Supernatant The test for desoxyribonuclease activity in sample aliquots was performed according to Kunitz, M., J. Gen. Physiol. 33 (1950) 349–62 and 363. Calf thymus DNA was dissolved at a concentration of 0.05 mg/ml in a buffer containing 10 mM TrisHCl pH 8.0, 0.1 mM $CaCl_2$, 1 mM $MgCl_2$. Purified desoxyribonuclease activity-containing growth medium such as culture supernatant was added and the increase of the extinction at 260 nm was photometrically measured over time at 25° C. 1 unit (1 U) corresponds to an extinction increase (ΔE) of 0.001 per min. Representative results are given in Table 1.

TABLE 1

Determination of desoxyribonuclease activity in the culture supernatant of three different transformed strains of *Pichia pastoris*

|  | Strain 1 | Strain 2 | Strain 3 |
|---|---|---|---|
| Assayed volume of culture supernatant | 0.01 ml | 0.007 ml | 0.007 ml |
| ΔE/min | 0.0114 | 0.0133 | 0.0155 |
| U/ml | 1,425 | 2,375 | 2,065 |

EXAMPLE 11

Assay to Determine the Specific Desoxyribonuclease Activity of Purified Bovine Pancreatic Desoxyribonuclease I The desoxyribonuclease-free reference sample was the sample buffer, that is a mixture of 1 part 1 M sodium acetate pH 5.0, 1 part 50 mM $MgSO_4$ and 8 parts double-distilled water. For the substrate buffer, calf thymus DNA was dissolved in a buffer containing 5 mM $MgSO_4$ and 100 mM sodium acetate pH 5.0 and incubated between 24 to 30 hours in a water bath at 37° C. Unsoluble parts were removed by centrifugation for 10 min at 13,000×g. Substrate buffer contained DNA at a concentration of 0.04 mg/ml. DNA content of the supernatant was determined photometrically at 260 nm and, if necessary, the substrate buffer was adjusted with sample buffer to give an extinction value of 0.8. Substrate buffer was stored for at least 3 days at 4° C. before use.

DNase-containing solution with a volume activity of about 10,000 units per ml obtained from purification of bovine pancreatic desoxyribonuclease I according to Example 9 was used for the determination of desoxyribonuclease activity. 5 μl of the desoxyribonuclease-containing solution was diluted with 95 μl double-distilled water. Firstly, 2.5 ml substrate buffer was filled into a quartz cuvette with a thtckness of 1 cm. Both the substrate buffer and the cuvette were kept at 25° C., measurements were at the same temperature. The wave length at which measurements were taken was 260 nm. After the photometer was set to zero extinction (reference value) 0.05 ml diluted desoxyribonuclease-containing solution was added and mixed. The increase of the extinction (ΔE/min) was measured over time. One unit (1U) corresponds to the activity that under the conditions as described above leads to an increase of the extinction of 0.001 per min.

The activity per volume given as was calculated as $$[U/ml] = \frac{2{,}55 \times 1{,}000 \times \Delta E/\min}{0.05}$$

The activity of undiluted bovine pancreatic desoxyribonuclease I preparations was calculated according to the dilution factor applied. It was also generally observed that the units measured using this assay were comparable to those of the Kunitz assay.

Additionally, protein content was measured using the same type of cuvettes as above. Measurements were taken of purified bovine pancreatic desoxyribonuclease I in sample buffer at temperatures between 20° C. and 25° C., at a wave length of 280 nm, with the sample buffer serving as reference.

The protein content was calculated from extinction values ($\Delta E_{280}$) as

[mg protein/ml]=$\Delta E_{280}$×0.796

Each measurement was taken in triplicate. Specific desoxyribonuclease activity in a given volume was then calculated as units per mg of protein. Representative results are given in Table 2.

TABLE 2

Determination of specific desoxyribonuclease activity of bovine pancreatic desoxyribonuclease I purified from the culture supernatant of three different multiply transformed strains of *Pichia pastoris*

|  | Strain 1 | Strain 2 | Strain 3 |
|---|---|---|---|
| Assayed volume of purified desoxyribonuclease preparation | 0.01 ml | 0.04 ml | 0.04 ml |
| ΔE/min | 0.008 | 0.011 | 0.0105 |
| U/ml | 99,375 | 17,266 | 16,328 |
| $\Delta E_{280}$ | 0.099 | 0.134 | 0.133 |
| mg of protein/ml | 15.8 | 2.13 | 2.1 |
| specific desoxyribonuclease activity | 6,289 | 8,106 | 7,775 |

EXAMPLE 12

Thermostability of Purified Active Bovine Pancreatic Desoxyribonuclease I

Aliquots of purified bovine pancreatic desoxyribonuclease I in a storage buffer containing 20 mM TrisHCl, 2 mM $MgCl_2$, 4 mM $CaCl_2$, 50% glycerol, pH 7.6 were incubated for 60 min at 55° C., 60° C., 65° C., 70° C., 75° C., and 80° C., whereby each aliquot had a volume of 500 μl and contained at least 10,000 units per ml. Each aliquot was kept over the heating period in a fine-regulated (variation limit less than 0.5° C.) thermostate block heater. Immediately after the incubation, residual specific desoxyribonuclease activity was measured as activity per volume using the assay as described in 0.

Representative results are tabulated in Table 3. Residual activity per volume after heat treatment is given as a percentage with the activity of an untreated control aliquot being set as 100%. No differences regarding heat stability were found with respect to *Pichia* yeast strains used for transformation (see e.g. Example 4) or the kind of signal peptides present in the respective pre-protein (see e.g. Examples 4, 6, 7, 8, 9).

TABLE 3

Residual specific desoxyribonuclease activity after heat incubation

| | Temperature | | | | | |
|---|---|---|---|---|---|---|
| | 55° C. | 60° C. | 65° C. | 70° C. | 75° C. | 80° C. |
| Residual specific desoxyribo-nuclease activity after 60 min | 91% | 86% | 73% | 58% | 52% | 46% |

LIST OF REFERENCES

Alberts, B., Johnson, A., Lewis, J., Raff, M., Roberts, K., Walter, P. (eds), Molecular Biology of the Cell, fourth edition, 2002, Garland Science Publishing
Beck, E., et al., Gene 19 (1982) 327–336
Carmels, T., et al., Curr. Genet. 20 (1991) 309–314
Chen, C. Y., et al., Gene 206 (1998) 181–184
Chen, X. J., and Fukuhara, H., Gene (1988) 181–192
Drocourt, D., et al., Nucleic Acids Res. 18 (1990) 4009
EP 0 116 201
EP 1 122 306
Funakoshi, A., et al., J. Biochem. (Tokyo) 88 (1980) 1113–1138
Julius, D., et al., Cell 37 (1984) 1075–1089
Kaighn, M. E., In: Tissue culture, methods and applications; Kruse, P. F. & Patterson, M. K., eds., Academic Press, New York & London, 1973, 54–58
Kunitz, M., J. Gen. Physiol. 33 (1950) 349–62 and 363
Lazarides, E., and Lindberg, U., Proc. Natl. Acad. Sci. USA 71 (1974) 4742
Liao, T. H., J. Formos. Med. Assoc. 96 (1997) 481–487
Liao, T. H., Mol. Cell Biochem. 34 (1981) 15–22
Nefsky, B., and Bretscher, A., Eur. J. Biochem. 179 (1989) 215–219
Nishikawa, A., and Mizuno, S., Biochem. J. 355 (2001) 245–248
Nishikawa, A., et al., J. Biol. Chem. 272 (1997) 19408–19412
Paudel, H. K., and Liao, T. H., J. Biol Chem. 261 (1986) 16006–16011
Sambrook, Fritsch & Maniatis, Molecular Cloning, A Laboratory Manual, 3rd edition, CSHL Press, 2001
Shak, S., Proc. Natl. Acad. Sci. USA 87 (1990) 9188–9192
Southern, P. J., and Berg, P., J. Mol. Appl. Genet. 1 (1982) 327–341
Thill, G. P., et al., Positive and Negative Effects of Multi-Copy Integrated Expression in *Pichia pastoris*, International Symposium on the Genentics of Microorganisms 2 (1990), pp. 477–490
U.S. Pat. No. 4,683,293
U.S. Pat. No. 4,808,537
U.S. Pat. No. 4,812,405
U.S. Pat. No. 4,818,700
U.S. Pat. No. 4,837,148
U.S. Pat. No. 4,855,231
U.S. Pat. No. 4,857,467
U.S. Pat. No. 4,870,008
U.S. Pat. No. 4,879,231
U.S. Pat. No. 4,882,279
U.S. Pat. No. 4,885,242
U.S. Pat. No. 4,895,800
U.S. Pat. No. 4,929,555
U.S. Pat. No. 5,002,876
U.S. Pat. No. 5,004,688
U.S. Pat. No. 5,032,516
U.S. Pat. No. 5,122,465
U.S. Pat. No. 5,135,868
U.S. Pat. No. 5,166,329
U.S. Pat. No. 5,324,639
U.S. Pat. No. 5,618,676
U.S. Pat. No. 5,854,018
U.S. Pat. No. 5,856,123
U.S. Pat. No. 5,919,651
van Treeck, U., et al., Antimicrob Agents Chemother. 19 (1981) 371–380
Vedvick, T., et al., J. Ind. Microbiol. 7 (1991) 197–201
Waters et al., J. Biol. Chem. 263 (1988) 6209–14
Werten, M. W., et al., Yeast 15 (1999) 1087–1096
WO 00/56903
WO 90/07572
WO 96/26278
Worrall, A. F., and Connolly, B. A., J. Biol. Chem. 265 (1990) 21889–21895

The invention claimed is:

1. A method of producing a bovine pancreatic protein with a specific desoxyribonuclease activity of at least 6,000 units per mg of protein purified in step (d), comprising the steps of
(a) providing a vector comprising a nucleotide sequence that encodes a pre-protein, the pre-protein comprising the bovine pancreatic protein and a signal peptide,
(b) transforming a methylotrophic yeast strain with the vector,
(c) cultivating the transformed methylotrophic yeast strain in a growth medium that comprises nutrients and methanol, whereby the methylotrophic yeast strain expresses and secretes the bovine pancreatic protein into the growth medium, and
d) purifying the bovine pancreatic protein from the growth medium.

2. The method according to claim 1, wherein the amino acid sequence of the bovine pancreatic protein is SEQ ID NO: 1.

3. The method according to claim 1 wherein the signal peptide further comprises a signal peptidase cleavage site which is located directly adjacent to the first amino acid of the bovine pancreatic protein.

4. The method according to claim 1 wherein the amino acid sequence of the expressed pre-protein is selected from the group consisting of SEQ ID NO: 2, SEQ ID NO: 3, and SEQ ID NO: 4.

5. The method according to claim 1, wherein the nucleotide sequence encoding the bovine pancreatic protein is SEQ ID NO: 5.

6. The method according to claim 1, wherein the nucleotide sequence encoding the pre-protein consists of the nucleotide sequence encoding the signal peptide fused to the nucleotide sequence encoding the bovine pancreatic protein.

7. The method according claim 5 wherein the nucleotide sequence encoding the signal peptide is selected from the group consisting of SEQ ID NO: 6, SEQ ID NO: 7, and SEQ ID NO: 8.

8. The method according to claim 1, wherein the nucleotide sequence encoding the pre-protein is operably linked to a promoter or promoter element.

9. The method according to claim 1, wherein the vector is a plasmid capable of being replicated as an episome in the methylotrophic yeast strain.

10. The method according to claim 1, characterised in that an artificial chromosome capable of being replicated in the methylotrophic yeast strain contains the vector.

11. The method according to claim 1, wherein a chromosome of the methylotrophic yeast strain contains the vector.

12. The method according to claim 1, wherein the methylotrophic yeast strain is *Hansenula, Pichia, Candida or Torulopsis* species.

13. The method according to claim 12, wherein the methylotrophic yeast strain is selected from the group consisting of *Pichia pastoris, Hansenula polymorpha, Candida boidinii* and *Torulopsis glabrata*.

14. A bovine pancreatic protein with a specific desoxyribonuclease I activity of at least 6,000 units per mg of protein-produced by the method of claim 1.

15. A kit containing a bovine pancreatic protein with a specific desoxyribonuclease activity of at least 6,000 units per mg of protein and a reaction buffer comprising a divalent cation.

16. A kit according to claim 15 wherein the bovine pancreatic protein is dissolved in a storage buffer containing water, glycerol, a protease inhibitor, and a divalent cation, wherein the reaction buffer contains a divalent cation selected from the group consisting of $Mg^{2+}$, $Ca^{2+}$ and $Mn^{2+}$.

17. The bovine pancreatic protein of claim 14 wherein the protein has a specific desoxyribonuclease I activity of about 6,000 to about 8,000 units per mg of protein.

18. A method of producing a bovine pancreatic protein comprising the steps of:
(a) providing a vector comprising a nucleotide sequence comprising the sequence of SEQ ID NO: 6 operably linked to the sequence of SEQ ID NO: 5 that encodes the bovine pancreatic protein of SEQ ID NO: 2,
(b) transforming a methylotrophic yeast strain with the vector,
(c) cultivating the transformed methylotrophic yeast strain in a growth medium that comprises nutrients and methanol whereby the methylotrophic yeast strain expresses and secretes the bovine pancreatic protein into the growth medium, and (d) purifying the bovine pancreatic protein from the growth medium.

19. The method of claim 18 wherein the signal peptide further comprises a signal peptidase cleavage site which is located directly adjacent to the first amino acid of the bovine pancreatic protein.

* * * * *